(12) United States Patent
Stuppner et al.

(10) Patent No.: US 8,765,804 B2
(45) Date of Patent: Jul. 1, 2014

(54) PHARMACEUTICAL COMPOSITIONS COMPRISING LIGNANS AND THEIR DERIVATIVES FOR TREATING HYPERPLASTIC DISEASES

(75) Inventors: Hermann Stuppner, Götzens (AT); Stefan Schwaiger, Innsbruck (AT); David Bernhard, Vienna (AT); Günther Laufer, Vienna (AT)

(73) Assignee: Universität Innsbruck, Innsbruck (AT)

( * ) Notice: Subject to any disclaimer, the term of this patent is extended or adjusted under 35 U.S.C. 154(b) by 352 days.

(21) Appl. No.: 13/054,385

(22) PCT Filed: Jul. 17, 2009

(86) PCT No.: PCT/EP2009/059256
§ 371 (c)(1),
(2), (4) Date: Apr. 19, 2011

(87) PCT Pub. No.: WO2010/007169
PCT Pub. Date: Jan. 21, 2010

(65) Prior Publication Data
US 2011/0189252 A1 Aug. 4, 2011

Related U.S. Application Data

(60) Provisional application No. 61/135,287, filed on Jul. 18, 2008.

(51) Int. Cl.
| | |
|---|---|
| *A01N 43/08* | (2006.01) |
| *A61K 31/34* | (2006.01) |
| *A01N 43/06* | (2006.01) |
| *A61K 31/38* | (2006.01) |
| *C07D 333/00* | (2006.01) |
| *C07D 409/00* | (2006.01) |
| *C07D 317/00* | (2006.01) |
| *C07D 323/02* | (2006.01) |
| *C07D 317/70* | (2006.01) |

(52) U.S. Cl.
USPC ............. 514/461; 514/438; 549/43; 549/429; 549/433

(58) Field of Classification Search
USPC ................. 514/461, 438; 549/43, 429, 433
See application file for complete search history.

(56) References Cited

U.S. PATENT DOCUMENTS

2005/0069577 A1* 3/2005 Diamond et al. ............. 424/450

FOREIGN PATENT DOCUMENTS

| CN | 1097992 | 2/1995 |
|---|---|---|
| WO | WO 2007/006492 | 1/2007 |

OTHER PUBLICATIONS

Back et al. "Leukotriene B4 signaling through NF-kB-dependent BLT1 receptors on vasuclar smooth muscle cells in atherosclerosis and intimal hyperlasia" PNAS, Nov. 2005, vol. 102, No. 48, pp. 17501-17506.*
Zhang et al. "Mechanisms of Intimal Hyperplasia Learned from Murine Carotid Artery Ligation Model" Current Vascular Pharmacology, Jan. 2008, vol. 6, pp. 37-43.*
Speroni et al., "In vivo efficacy of different extracts of Edelweiss (*Leontopodium alpinum* Cass.) in animal models," *J. Ethnophannacol*, 105:421-6, 2006.
International Search Report, issued in International Patent Application No. PCT/EP2009/059256, dated Oct. 9, 2009.
Dobner et al., "Anti-inflammatory activity of *Leontopodium alpinum* and its constituents," *Planta. Med.*, 70:502-8, 2004.
Schwaiger et al., "New constituents of *Leontopodium alpinum* and their in vitro Leukotriene biosynthesis inhibitory activity," *Planta. Med.*, 70:978-85, 2004.
Speroni et al., "In vivo efficacy of different extracts of Edelweiss (*Leontopodium alpinum* Cass.) in animal models," *J. Ethnopharmacol.*, 105:421-6, 2006.
Wang et al., "Specific anticancer activity of a new bisabolane sesquiterpene against human leukemia cells inducing differentiation in vitro," *Pharmazie*, 62:699-704, 2007.

* cited by examiner

*Primary Examiner* — Kendra D Carter
(74) *Attorney, Agent, or Firm* — Parker Highlander PLLC

(57) ABSTRACT

The present invention relates to a pharmaceutical composition comprising specific compounds which may be obtained from *Leontopodium alpinum* Cass. (Edelweiss). A preferred compound is leoligin (=(2S,3R,4R)-4-(3,4-dimethoxybenzyl)-2-(3,4-dimethoxyphenyl)tetrahydrofuran-3-yl]methyl (2Z)-2-methylbut-2-enoat]). Corresponding means and methods in respect of medical uses of the compounds are described. The present invention also provides a medical device comprising, containing or having been contacted with the compound. The compounds provided herein may particularly be used in the treatment of hyperplastic diseases, in particular intimal hyperplasia, e.g. stenosis, restenosis, atherosclerosis and the like. Also envisaged herein is the use of these compounds in the treatment of proliferative diseases, such as leukemia, prostate cancer and lung cancer.

10 Claims, 14 Drawing Sheets

Figure 1:
Figure 1:
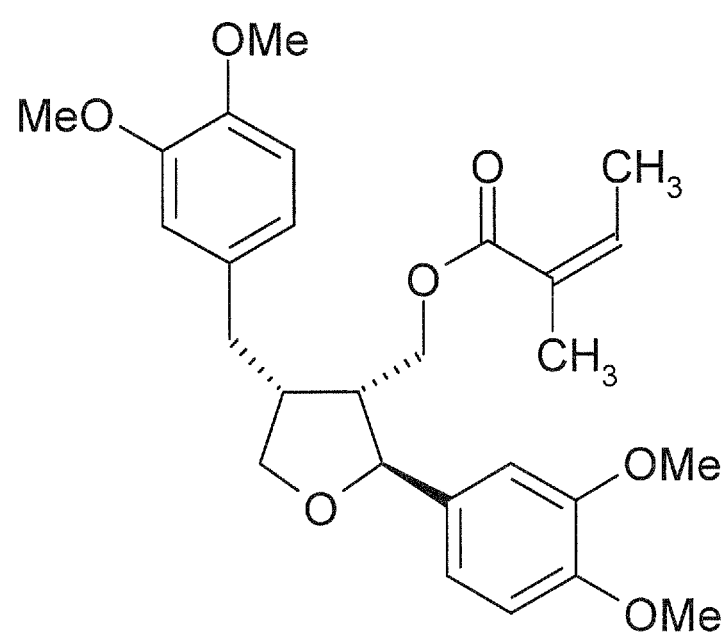

A.

B.

A.

B.

A.

B.

C.

A.

B.

C.

A.

B.

PHARMACEUTICAL COMPOSITIONS COMPRISING LIGNANS AND THEIR DERIVATIVES FOR TREATING HYPERPLASTIC DISEASES

The present application is a national phase application under 35 U.S.C. §371 of International Application No. PCT/EP2009/059256 filed Jul. 17, 2009 which claims priority to US Provisional Application No. 61/135,287 filed Jul. 18, 2008 the entire text and figures of which disclosures are incorporated herein by reference without disclaimer.

The present invention relates to a pharmaceutical composition comprising specific compounds which may be obtained from *Leontopodium alpinum* Cass. (Edelweiss), or structurally related compounds. A preferred compound is leoligin (=(2S,3R,4R)-4-(3,4-dimethoxybenzyl)-2-(3,4-dimethoxyphenyl)tetrahydrofuran-3-yl]methyl(2Z)-2-methylbut-2-enoat]). Corresponding means and methods in respect of medical uses of the compounds are described. The present invention also provides a medical device comprising, containing or having been contacted with the compound. The compounds provided herein may particularly be used in the treatment of hyperplastic diseases, in particular intimal hyperplasia, e.g. stenosis, restenosis, atherosclerosis and the like. Also envisaged herein is the use of these compounds in the treatment of proliferative diseases, such as leukaemia, prostate cancer and lung cancer.

Coronary artery bypass grafting (CABG) and percutaneous coronary intervention (PCI) are the two invasive options to treat coronary artery disease (CAD), being one of the leading causes of morbidity and mortality worldwide; see WHO, Cardiovascular diseases, Internet Communication (2007); see also www.who.inticardiovascular_diseases/en/. The success of both therapeutic approaches is however often limited by restenosis and graft failure which are considered as hyperplastic diseases/disorders. With respect to graft patency rates after CABG the vessels of choice are clearly the internal mammary arteries; see Tatoulis, *Ann Thorac Surg*, 77(1), 93-101 (2004). However due to limitations in availability saphenous vein grafts are more frequently used in CABG than arterial grafts (e.g. in 2004 at the Innsbruck Medical University 51% of bypass grafts were saphenous veins; see Schachner, *European Surgery* 39(2), 72-5 (2007). In past years clinical optimization, like graft handling (e.g. "no touch techniques") and lipid lowerine, therapy has impressively increased the patency rates of saphenous vein conduits and is currently approximately at 60% 10 years after CABG (Schachner (2007) loc. cit; Lau. *Semin Vase Med* 4(2), 153-9 (2004); Tsui, *Eur J Vase Endovasc Surg* 23(3), 202-8 (2002). Still, the major reasons for a loss of patency at earlier time points are thromboses, neointima formation. and intimal hyperplasia, (10-20% loss of patency after the first year), and graft atherosclerosis later after CABG (Lau (2004), loc. cit.; Hozumi, *Heart* 76(4), 317-20 (1996); Marin, *J Vase Surg* 18(3):407-14 (1993). Thus, graft disease still significantly limits the durability of venous bypasses.

Generally, the causative factors and the pathophysiological processes that underlie vein graft disease are not well understood. It is thought that vein graft disease is a result of a variety of events initiated by vascular damage that does occur due to surgical handling, ischemia, and arterialisation (blood pressure, blood flow) of grafts. This initial damage is though to provoke adaptive repair processes in the vessel wall, like tissue remodelling (positive and negative) and intimal hyperplasia; see Lau (2004), loc. cit., Hozumi (1996), loc. cit., Marin (1993), loc. cit; Lau, *Circulation* 4, 114(1 Suppl):I435-I440 (2006). On one hand this response is vital for the adaptation of the graft to the arterial environment, but an excessive response is thought to give raise to graft disease that ultimately results in graft failure.

Despite a complex array of intra and inter cellular signalling events in the development of graft disease after CABG and/or PCI the core elements on the histological level are endothelial damage (denudation) and smooth muscle cell (SMC) proliferation and infiltration of the intima. Pro-inflammatory signalling due to tissue damage and cellular necrosis but also as an element of adaptive tissue remodelling is another highly relevant factor; see Mitra, *Immunol Cell Biol* 84(2), 115-24 (2006). Although, the excellent concept of using drug eluting stents/matrices instead of purely mechanical devices will most likely prevail in PCI- and CABG-based prevention of restenosis and graft failure, at the moment there is a significant lack of functional drugs, screened or designed precisely for these applications. Currently used drugs are mainly chemotherapeutic agents developed for cancer or immunosuppressive therapy, which may be too aggressive or unspecific for the treatment of restenosis and graft disease, since also endothelial, healing—important for the prevention of thromboses—is impaired by these drugs.

Lignans are considered as potential candidate molecules which may be used in the treatment of diseases/disorders associated with the cardiovascular system and will be discussed herein below in more detail. However, only a limited number of publications have reported on the impact of lignans on the cardiovascular system in general, and only a few different lignans have been tested so far. It is of note that a treatment of hyperplastic diseases/disorders with lignans has not been described in the art. The existing data rather suggest that lignans are cardiovascular protective agents with lipid lowering, anti-oxidative, anti-hypertensive, anti-thrombotic, and anti-inflammatory activities.

A large number of lignan-based cancer therapy studies (in vitro and in vivo) showed profound cytotoxicity and cell death induction by these compounds, see Kim *Planta Med*, 68(3), 271-4 (2002) and *J Cell Biochem* 84(3), 532-44 (2002). The use of cytotoxic compounds in the treatment of a hyperplastic disease/disorder, and in particular vein graft disease, is generally considered as detrimental since also healthy cells, such as EC cells can be damaged. Hence, the use of cytotoxic lignans known in the art should be avoided in the treatment of these diseases. Therefore, there is still a demand for compounds which may be used in the treatment of hyperplastic diseases/disorders and which avoid the disadvantages of compounds known in the art.

Thus, the technical problem underlying the present invention is the provision means and methods for the medical interference in hyperplastic diseases or hyperplastic disorders.

The technical problem is solved by provision of the embodiments characterized in the claims.

Accordingly, the present invention relates to a pharmaceutical composition comprising a compound of formula (I)

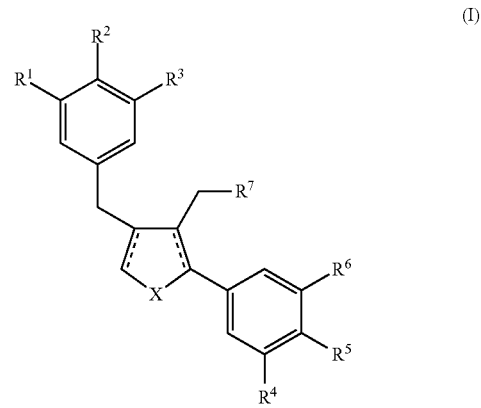

wherein

R$^1$, R$^2$ and R$^3$ are independently selected from H, OH, halogen, alkyl, or alkoxy; and R$^4$, R$^5$ and R$^6$ are independently selected from H, OH, halogen, alkyl, or alkoxy;

R$^7$ is selected from —OR$^8$, —N(R$^{8'}$)R$^8$, —SR$^8$, —C(O)R$^8$, —OC(O)R$^9$, —C(O)OR$^9$, —N(R$^{9'}$)C(O)R$^9$, —C(O)N(R$^{9'}$)R$^9$ or —S(O)R$^9$; wherein R$^8$ and R$^9$ are independently selected from alkyl or alkenyl and R$^{8'}$ and R$^{9'}$ are independently selected from H, alkyl or alkenyl; and wherein any alkyl or alkenyl group comprised in R$^7$ may be unsubstituted or substituted by one or more substituents, selected from OH, halogen or alkoxy;

X is selected from O, S, C(R$^{10}$)R$^{10}$ and NR$^{10}$ wherein R$^{10}$ is H, alkyl or alkenyl;

and the dashed lines in the ring structure containing group X indicate that the respective bond may be a single or a double bond;

or any pharmaceutically acceptable salt or solvate thereof.

In a preferred embodiment, the compound of formula (I) comprised in the pharmaceutical composition has the stereochemistry indicated in formula (Ia):

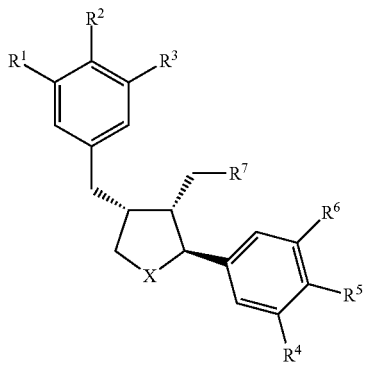

(Ia)

wherein R$^1$ to R$^7$ and X are defined as described herein above.

For the above formulae (I) and (Ia), the following embodiments are preferred in the context of the invention.

Alkyl substituents, as they may be present as R$^1$ to R$^6$, are preferably C1 to C6 alkyl groups, more strongly preferred are C1 to C3 alkyl groups, and further preferred is methyl.

Halogen substituents include fluoro-, chloro-, bromo- and iodo-atoms, with preference given to chloro and bromo.

As set out above, X is selected from O, S, C(R$^{10}$)R$^{10}$ and NR$^{10}$; wherein R$^{10}$, independently for each occurrence, is H, alkyl or alkenyl. Preferred as alkyl group is a C1 to C6 alkyl group, particularly preferred are methyl and ethyl. Preferred as an alkenyl group is a C2 to C6 alkenyl group.

Preferably, X is O or NR$^{10}$, and particularly preferred is O. Preferred groups R$^{10}$ are H and C1 to C6 alkyl, particularly preferred are H and methyl.

As further explained above, the dashed lines in the ring structure containing group X indicates that the respective bond may be a single or a double bond. The ring structure may contain no double bond, one double bond or two double bonds at the respective position. Preferred are cases where no double bond is present, i.e. the ring structure containing group X is a saturated ring.

It is generally preferred that at least one of R$^1$ to R$^3$ represents an alkoxy group, and it is more preferred that two or all three of them represent an alkoxy group. Among suitable alkoxy groups, general preference is given to C1 to C6 alkoxy groups, more strongly preferred are C1 to C3 alkoxy groups and particular preference is given to methoxy groups. If two of R$^1$ to R$^3$ represent an alkoxy group, it is preferred that one of them is R$^2$.

In the preferred compounds referred to above, wherein one or two of R$^1$ to R$^3$ represent an alkoxy group, it is further preferred that the remaining groups of R$^1$ to R$^3$ represent H or an alkyl group, preferably H. Preferred alkyl groups are C1 to C6 alkyl groups, more strongly preferred are C1 to C3 alkyl groups, and further preferred is methyl.

It is generally preferred that at least one of R$^4$ to R$^6$ represents an alkoxy group, and it is more preferred that two or all three of them represent an alkoxy group. Among suitable alkoxy groups, general preference is given to C1 to C6 alkoxy groups, more strongly preferred are C1 to C3 alkoxy groups and particular preference is given to methoxy groups. If two of R$^4$ to R$^6$ represent an alkoxy group, it is preferred that one of them is R$^5$.

In the preferred compounds referred to above, wherein one or two of R$^4$ to R$^6$ represent an alkoxy group, it is further preferred that the remaining groups of R$^4$ to R$^6$ represent H or an alkyl group, preferably H. Preferred alkyl groups are C1 to C6 alkyl groups, more strongly preferred are C1 to C3 alkyl groups, and further preferred is methyl.

Thus, particularly preferred are compounds wherein four, five or all six of R$^1$ to R$^6$ are alkoxy, and the remaining groups of R$^1$ to R$^6$, if any, are hydrogen. Mention may be made in this respect specifically of compounds wherein R$^1$ is H and R$^2$ and R$^3$ are alkoxy, or all of R$^1$ to R$^3$ are alkoxy; and wherein R$^4$ is H and R$^5$ and R$^6$ are alkoxy, or all of R$^4$ to R$^6$ are alkoxy. Among suitable alkoxy groups, general preference is given to C1 to C6 alkoxy groups, more strongly preferred are C1 to C3 alkoxy groups and particular preference is given to methoxy groups.

R$^7$ is preferably —OC(O)R$^9$, —C(O)OR$^9$, —N(R$^{9'}$)C(O)R$^9$, —C(O)N(R$^{9'}$)R$^9$ or —S(O)R$^9$, i.e. an ester, amide or sulfoxy group, with a particular preference for the ester groups —OC(O)R$^9$ or —C(O)OR$^9$. Most preferred as R$^7$ is a group —OC(O)R$^9$.

R$^8$ is preferably an alkyl or alkenyl group which is unsubstituted. Preferred alkyl groups have 2 or more, particularly 3 or more carbon atoms. It is further preferred that they have 14 or less, such as 10 or less, particularly 8 or less or 6 or less carbon atoms. Preferred alkenyl groups have 3 or more carbon atoms. It is further preferred that they have 14 or less, such as 10 or less, particularly 8 or less or 6 or less carbon atoms. Independent of the number of carbon atoms, it is preferred that the alkenyl groups have one C—C double bond.

R$^{8'}$ is preferably H or any alkyl group having 10 or less, such as 8 or less, preferably 6 or less carbon atoms, such as methyl, ethyl, or propyl.

R$^9$ is preferably an alkyl or alkenyl group which is unsubstituted. Preferred alkyl groups have 2 or more, particularly 3 or more carbon atoms. It is further preferred that they have 14 or less, such as 10 or less, particularly 8 or less or 6 or less carbon atoms. Preferred alkenyl groups have 3 or more carbon atoms. It is further preferred that they have 14 or less, such as 10 or less, particularly 8 or less or 6 or less carbon atoms. Independently of the number of carbon atoms, it is preferable that the alkenyl groups have one C—C double bond. Particularly preferred as R$^9$ is a branched alkenyl group as it occurs in leoligin of the formula —C(CH$_3$)CH—CH$_3$. In this group. the methyl substituents at the double bond may be in E- or Z-configuration with respect to each other, with preference for the Z-configuration.

$R^{9'}$ is preferably H or any alkyl group having 10 or less, such as 8 or less, preferably 6 or less carbon atoms, such as methyl, ethyl. or propyl.

In a strongly preferred embodiment, the present invention concerns pharmaceutical compositions comprising compounds of formula (1) or (1a) wherein X is O; wherein, in the case of formula (1), the ring structure containing X has no double bonds; wherein four, five or all six of $R^1$ to $R^6$ are alkoxy, and the remaining groups of $R^1$ to $R^6$, if any, are hydrogen.; $R^7$ is —OC(O)$R^9$ or —C(O)O$R^9$, particularly —OC(O)$R^9$; and $R^9$ is an unsubstituted alkenyl group having one double bond and 8 or less carbon atoms or an unsubstituted alkyl group having two or more and 8 or less carbon atoms.

While the invention has been described as relating to pharmaceutical compositions, it should be understood that the compounds contained in these pharmaceutical compositions as active agents play an important role in the context of the invention. Thus, the claims also encompass preferred compounds per se, such as the compounds of formula (1) or (1a) defined above, wherein five or all six of $R^1$ to $R^6$ are alkoxy; the remaining group of $R^1$ to $R^6$, if applicable, is hydrogen; and the ring structure containing X, the group X and $R^7$ are as defined above, including preferred embodiments thereof.

A further strongly preferred embodiment relates to a pharmaceutical composition, wherein the compound of formula (I) has the following structure:

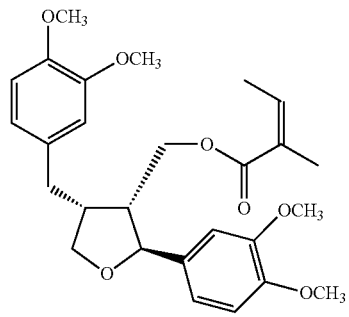 [SMILES: C/C=C(/C)C(=O)OC[C@H]1[C@@H](Cc2ccc(OC)c(OC)c2)CO[C@@H]1c1ccc(OC)c(OC)c1]

The chemical structure given herein above is (2S,3R,4R)-4-(3,4-dimethoxybenzyl)-2-(3,4-dimethoxyphenyl)tetrahydrofuran-3-yl]methyl (2Z)-2-methylbut-2-enoat] also commonly known under the trivial name "leoligin". Leoligin has been shown in the appended examples as a particularly strong inhibitor of cell proliferation, in particular proliferation of SMCs. It is known that proliferation of SMCs is a central mechanism specifically involved in a hyperplastic disease/disorder, in particular intimal hyperplasia. Proliferation of SMCs is also involved in vein graft disease, which will be described herein below in more detail.

The present invention solves the above identified technical problem since, as documented herein below and in the appended examples, it was surprisingly found that a lignan derived from the roots of Edelweiss (*Leontopodium alpinum* Cass.), namely leoligin [(2S,3R,4R)-4-(3,4-dimethoxybenzyl)-2-(3,4-dim ethoxyphenyl)tetrahydro furan-3-yl]methyl (2Z)-2-methylbut-2-enoat] and derivatives thereof exhibit a highly beneficial effect in a medical setting. Leoligin has been shown herein to be a stronger inhibitor of vascular smooth muscle cell (SMC) proliferation compared to other compounds known in the art, such as lariciresinol (see in particular Example 2 and FIG. 6; formula given herein below).

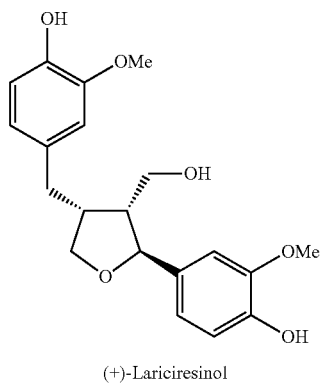 [SMILES: COc1cc(C[C@H]2CO[C@H](c3ccc(O)c(OC)c3)[C@H]2CO)ccc1O]

(+)-Lariciresinol

Isolated primary human vascular smooth muscle cells represent the central cell type in intimal thickening and intimal hyperplasia. Thus, SMC proliferation and migration is a central mechanism underlying hyperplastic diseases/disorders and inhibitors of this mechanism may interfere with the development and/or progression of theses diseases.

Another, even more surprising finding was that not only leoligin but compounds of formula (I) in general and leoligin derivatives as described herein inhibit vascular smooth muscle cell (SMC) proliferation. Some derivatives of leoligin, such as the 5-methoxy- and 5,5'-dimethoxy-derivative, inhibit SMC proliferation at a comparable or at even lower concentration than leoligin, see Example 3 and FIG. 7. In contrast thereto, lariciresinol (IC$_{50}$>100 µM) induced a weak inhibition of SMC when compared to leoligin (IC$_{50}$=54.5 µM), and its 5-methoxy-derivatives, e.g. 5-methoxy-leoligin (IC$_{50}$=45.9 µM) and 5,5'-dimethoxy-derivatives, e.g. 5,5'-dimethoxy-leoligin (IC$_{50}$=48.6 µM) after 72 h. Without being bound by theory, it is believed that the methoxy-groups may contribute to an increase in lipophilicity of the compounds to be used in accordance with the present invention, thus possibly enhancing and/or facilitating their cellular uptake. This may be one reason why e.g. 5-methoxy-derivatives of leoligin can be used at comparable or lower concentrations than leoligin.

Structural formulas of exemplary methoxy-derivatives and dimethoxy-derivatives, which also represent preferred compounds in the context of the present invention, are given herein below:

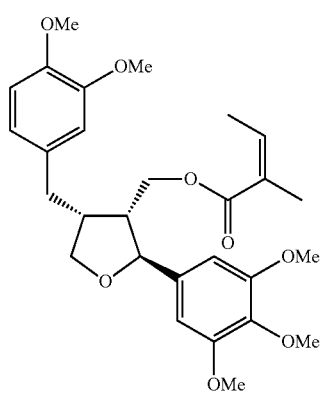

5-Methoxy-Leoligin

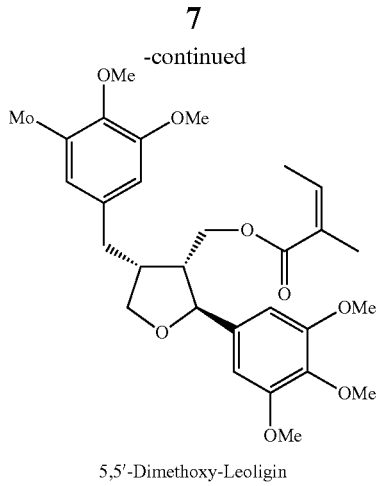

5,5'-Dimethoxy-Leoligin

A further advantage of the compound comprised in the pharmaceutical composition of the present invention, in particular leoligin and derivatives thereof, is its property not to induce cell death in SMCs, and most importantly also not in endothelial cells (ECs). Endothelial cells form a thin layer of cells, the so called endothelium, that line the interior surface of blood vessels. The endothelium forms an interface between the circulating blood and the rest of the vessel wall. Proper endothelial function is essential for blood vessel integrity and loss of its function is a hallmark for vascular diseases.

The property of the compounds to be used in accordance with the present invention not to induce cell death is in strong contrast to compounds known in the art, where cytotoxic effects were observed, e.g. the lignans honokiol and magnolol described herein below. In contrast, the compounds provided herein represent lignans which differ from known lignans by the lack of toxicity and cell death-inducing activity and also by their cell cycle inhibitory activity. The compounds of the present invention are therefore of particular advantage in the treatment of (a) hyperplastic disease(s)/disorder(s).

In the appended experimental section herein below it is shown that the compounds of the present invention comprised in a pharmaceutical composition can successfully be used as inhibitor of intimal hyperplasia in a human saphenous vein organ culture model for graft disease. The compounds and in particular leoligin, potently inhibited intimal hyperplasia, and even reversed graft disease in pre-damaged vessels. In a mouse model for venous bypass graft disease leoligin potently inhibited intimal hyperplasia in vivo, and had no negative effect on the integrity of the vascular endothelium. Such an assessment can also be carried out in larger animals/animal models. An exemplary protocol is provided in the experimental section herein below. In particular, an exemplary protocol using a porcine animal model (i.e. "Landschwein") to assess the efficacy of the particular compound known under the trivial name "Leoligin" is given in the appended examples. Pigs (such as the well-known "Landschwein", a particular pig race) are a preferred animal model of (bypass-) intimal hyperplasia and stenosis to be used in context of the present invention, since the circulatory system of pigs is very similar to that of humans. A person skilled in the art is readily in the position to adapt this protocol (e.g. to compounds of formula (I), in particular to (a) (di)methoxy-derivative(s) of leoligin (in various concentrations) or to other large animal models) and assess that compounds of formula (I) as described herein inhibit intimal hyperplasia also in large animals in vivo. It is apparent from the above that results obtained in pigs can, to a large extent, be extrapolated to humans.

The following parameters/effects define independently of each other a treatment success evaluated for example by the above animal models (e.g. porcine model) of compounds of formula (I), in particular Leoligin (and/or its ((di)methoxy-) derivative(s): 1) An intima thickness and/or intima-media thickness of the treatment group below the control group. 2) A smaller number of smooth muscle cells in the intima of the treatment group compared to the control. 3) The presence of a higher number of p27 and or p21 positive cells in the treatment group compared to the control. 4) A smaller degree of neointima formation in the treatment group compared to the control. 5) A reduced presence of tissue remodelling processes in the treatment group compared to the control. 6) A lower number of pro-inflammatory cells in the vessel wall in the treatment group compared to the control. 7) An intact endothelium. 8) A physiological degree of contractility of the vessels. 9) A low degree of adhesion molecule expression on the endothelial surface. 10) patency of grafts and no signs of thrombus formation. 10) Conserved elasticity of grafts in the treatment group compared to the control. And 11) Conserved contractility of grafts in the treatment group compared to the control.

In the prevention of vein graft failure after CABG the major therapeutic targets are neointima formation and intimal hyperplasia (early to intermediate complications) as well as graft atherosclerosis (long term complication). Although some progress has been made in past years a major limit in current strategies is the lack of appropriate compounds, as mentioned above. Most of the applied agents are too aggressive, and often cause not only SMC apoptosis and inhibition of proliferation, but also significantly reduce endothelial viability. Since the closure of the vascular endothelium after PCI or CABG is very important in vascular healing and anti-thrombosis, compounds that are not toxic for ECs are interesting agents for intra- and extravascular drug eluting stents and matrices. The compounds provided herein and in particular leoligin have exactly this active profile. Although leoligin inhibits EC proliferation (see FIG. 4), which may reduce local endothelial healing, a wound repair via the circulation (EC precursors and circulating ECs) is possible (see FIG. 5). The reason for this in vivo observation may be due to the fact that leoligin is not toxic for ECs, which could facilitate a re-colonisation of denuded vessel areas, and consequently reduce thromboses. Compounds of formula (I) and, in particular leoligin and ((di)methoxy)derivatives thereof may be advantageously used in the treatment, prevention and amelioration of (a) hyperplystic disease(s)/disorder(s), in particular intimal hyperplasia and thromboses in CABG and PCI.

In sum, it has been surprisingly found in the context of the present invention that compounds of formula (I) as described herein above, such as leoligin and ((di)methoxy)derivatives thereof, can successfully be used in a medical setting for the inhibition of cellular proliferation, in particular the proliferation of SMCs. In contrast to compounds known in the art, the compounds of the present invention are non-toxic and can be used at low concentrations. Thus, the pharmaceutical composition of the present invention comprising these compounds is particularly useful in the treatment of hyperplastic diseases/disorders, in particular intimal hyperplasia, such as vein graft disease. The compounds may—due to their EC preserving character—also be applied in drug eluting stents.

Such a beneficial use of these compounds in a medical setting has not been described in the art, even though anti-angiogenic activity of some lignans was reported; see Bai, *J Biol Chem* 278(37), 35501-7 (2003) and Bergman *Clin Can-* cer Res 13(3), 1061-7 (2007). However, these lignans are structurally different from the compounds provided in the present invention.

For example, lignans to be used in the prior art are honokiol and magnolol which are derived from *Magnolia* species. The respective formulas are given herein below:

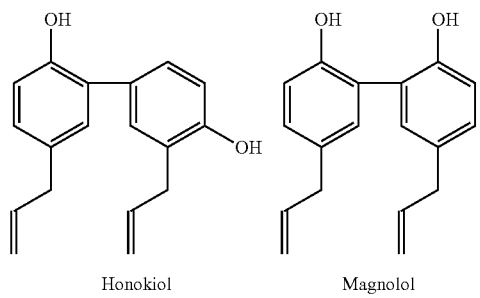

Honokiol          Magnolol

It is evident from these formulas that neither honokiol nor magnolol have a structural similarity to the compound to be used in context of the present invention. Honokiol, a lignan constituent of the plant *Magnolia officinalis*, was shown to inhibit cell death in ECs but also to potentiate cell death in vivo and in vitro; see Zhang, *Eur J Pharmacol,* 554(1), 1-7 (2007) and Ahn, *Mol Cancer Res* 4(9), 621-33 (2006). Honokiol was further shown to caused an arrest in the G1 phase of the cell cycle in SMCs which was associated by an upregulation of p21/WAF1; see Lee (2006), loc. cit. Magnolol, another lignan isolated from *Magnolia officinalis* was shown to induce cell death in SMCs in a capase-dependent manner and also to inhibit TNFalpha-mediated VCAM-1 expression as well as to prevent IL-6-induced STAT3 expression in ECs; see Chen, *Naunyn Schmiedebergs Arch Pharmacol* 368(2). 127-33 (2003); Chen, *Br J Pharmacol* 135(1), 37-47 (2002); Chen *Br J Pharmacol* 148(2), 226-32 (2006), A study by Razuvaev (*J Vasc Surg* 46(1), 108-15 (2007)) reported that the cyclolignan picropodophyllin inhibits intimal hyperplasia after balloon injury in vivo via an interaction with IGF-receptor and ERK signalling. However, a potential toxicity of picropodophyllin on endothelial cells has not been tested. A few other lignan type compounds, like flax seed lignans have been tested in different model systems of inflammation, cancer, and cardiovascular diseases. Due to a lack of knowledge concerning specificities and characteristics of different lignans however the mechanisms underlying the interaction of lignans with the cardiovascular system are not well defined.

Without being bound by theory, one mechanism by which the compound of the present invention may exert its effect in a medical setting is its induction of a cell cycle arrest in the G1-phase, which is associated by an accumulation of the cell cycle inhibitor p27/KIP. The underlying mechanism of the effect conferred by the compound used and provided in accordance with the present invention may be its induction of an arrest in the cell cycle. In contrast to honokiol which causes a cell cycle arrest in the G1 phase by an upregulation of p21 (see Lee, *FEBS Lett* 580(2), 5177-84 (2006)), leoligin leads to an increase in p27/KIP protein levels. Although the result i.e. a G1 phase arrest is similar for both compounds, the underlying signalling processes involved, and the mechanism of action may differ. P27/KIP is well known to bind and thereby inactivate the cyclinE/cdk2 complex which phosphorylates pRB. Phosphorylated pRB looses its ability to inhibit transcription factors like E2F, which upon release serve as transcription factors for proliferation-promoting genes. Although p27/KIP was also reported to cause an arrest at the G2-S transition in a limited number of cell types via an interference with cyclinA/cdk2 and cyclinB/cdk2 complexes (see Pagano, *Mol Cell* 14(4), 414-6 (2004)), in the case of SMCs the usually observed interaction of p27/KIP with cyclinE/cdk2 complexes which leads to an arrest in the G1 phase seems to be at play. The shift in the molecular weight of p27/KIP-1 at 50 μM leoligin from 27 kD to 58 and 85 kD respectively, may indicate the binding of p27/KIP-1 to the cyclinE/cdk2 complex, or an oligomerisation of molecules (dimers/trimers). The 23 kD band may represent a cleavage product of p27/KIP. The signalling pathways via which leoligin leads to the accumulation and change in molecular weight of p27/KIP-1 protein remain to be elucidated.

Only recently, Edelweiss root extracts have been chemically characterized; see Dobner et al. (2003), loc. cit. Edelweiss root extracts show a complex pattern of secondary plant metabolites, of several compound classes like coumarins, lignans, sesquiterpenes, polyacetylens, diterpenes, and others: see Schwaiger, *Planta Med,* 70(10), 978-85 (2004). In general, lignans are polyphenolic plant metabolites derived from phenylalanine, which are synthesized by the coupling of two phenylpropanoid units by a bond between the (3-positions in the propane side chains. One of these lignans which has been isolated from the roots of Edelweiss is leoligin —IUPAC name [(2S,3R,4R)-4-(3,4-dimethoxybenzyl)-2-(3, 4-dimethoxyphenyl)tetrahydrofuran-3-yl]methyl (2Z)-2-methylbut-2-enoat]. Although it is thus known that roots of Edelweiss (*Leontopodium alpinum* Cass.), one of the most popular alpine plants, which has been used in folk medicine for the treatment of diarrhoea, fever, and "abdominal aches" contain lignans, a medical use of any of these lignans, and in particular leoligin and its ((di)methoxy)derivatives, as an inhibitor of cellular proliferation, in particular the proliferation of SMCs, has neither been described nor proposed in the art. Also a medical use of the isolated compounds of the general formula (I) as given herein above, has not been described in the prior art.

As mentioned above, edelweiss and extracts thereof have been used in folk medicine. However, it is of note that only the upper parts (i.e. flowers, leaves and stems) of the Edelweiss plant have been used because these contain the bulk of the biomass and have thus been easier available. Historical references from the year 1582 mention that Edelweiss and its relatives are mainly used for the treatment of diarrhoea and dysentery; see Tabernaemontanus, J. T. (1582): Das Ander Buch von Kreutern. In: Bauhin, H. (ed.) (1731): D. Jacobi Theodori Tabernaemontani neu vollkommen Kraeuter-Buch. Reprint Basel, König, 1731. Verlag Kölbl, Grünwald (München) 1993). Further information on the traditional use of Edelweiss was collected by several diploma theses on the usage of Alpine plants in folk medicine, performed at the Institute of Pharmacognosy of the University of Vienna. Interviews of elder inhabitants of alpine regions in Austria and Northern Italy revealed a variety of local knowledge. In Vorarlberg Edelweiss flower heads were boiled in milk, preparations of which were used for the therapy of abdominal aches and diarrhoea in humans, and particularly also in domestic stock; see Kiene, Volksmedizin in verschiedenen Gebieten Vorarlberg, Master Thesis at the University of Vienna (1992); Bitschnau, Arzneidrogen der Volksmedizin im Montafon, Master Thesis at the University of Vienna (1991).

Similar information was also obtained for North-Tyrol, East-Tyrol and South-Tyrol, where Edelweiss was, furthermore, used to cure tonsillitis, angina and bronchitis, and as an antipyretic to lower fever; see Knechtl, Volksmedizinisch verwendete Heilpflanzen und Hausmittel im Inntal und umgebenden Seitentälern (Tirol), Master Thesis at the University of Vienna (1992); "Wieser, Volksmedizinische Verwendung von Heilpflanzen und Hausmitteln im Osttiroler Pustertal mit Seitentälern und im Lesachtal", Master Thesis at the University of Vienna (1995); Pickl-Herck, Volksmedizinische Anwendung im Norden Südtirols. Master Thesis at the University of Vienna (1995). In Polish traditional medicine, *L. alpinum* was used for the therapy of breast cancer by local application of a poultice of the aerial plant parts; see Hartwell. J. Nat. Prod. (Lloydia) 31, 71-170 (1968). Knechtl (1992; loc. cit.) also describes that infusions of edelweiss flowers can be used to ameliorate stomach-ache. In particular diarrhea in children is to be treated with milk in which flowers from edelweiss plants has been boiled; see Knechtl (1992; loc. cit.). Wieser (1995; loc. cit.) points out that upper parts of edelweiss plants are used in folk medicine, since edelweiss plants are selected out of the cut grass of alpine meadows (i.e. the upper parts of edelweiss plants are collected) and dried. This has been particularly described for the Villgratental in Kalkstein (1650 m above sea level). The edelweiss plant is described in Wieser (1995; loc. cit.) as the "camomile" of the Alps, since it is used in medicine similar to camomile. According to Wieser (1995; loc. cit.) an edelweiss infusion is used to ameliorate stomach ache, while edelweiss boiled in milk is helpful in abdominal cramping. Pickl-Herk (1995; loc. cit.) describes the following medical use of edelweiss flowers: infusion of flowers is beneficial in ameliorating stomach ache (in particular caused by foul drinking water), stomach flatulencies, and diarrhoea with vomiting. Again, infusions of edelweiss flowers are intended to be administered in particular to children. "Edelweissmilch" (i.e. 4-5 flowers boiled in 0.5 l milk) is used for the following disorders: diarrhea, vertigo, poisoning (leads to vomiting), snakebites, blood poisoning, indigestion, abdominal cramping, stomach ache, stomach flatulencies, or hangover; see Pickl-Herk (1995; loc. cit.). Also the use of "Edelweissmilch" in veterinary medicine is disclosed in this document, i.e. the treatment of calves suffering from diarrhoea and of calves/cows suffering from stomach flatulencies is described.

Again, the use of Edelweiss in folk medicine as described in the prior art documents above involves only extracts from the upper parts of the plant, but not of the roots. Also a specific compound contained in this extract to be used in folk medicine has not been described in this context.

As mentioned above and shown in detail in the experimental section herein below, the compound to be used in accordance with the present invention or the compound as comprised in the pharmaceutical composition of the present invention may be obtained from plants belonging to the genus *Leontopodium*, optionally followed by standard derivatization reactions. It is particularly preferred that the compounds provided herein may be obtained from *Leontopodium alpinum*, in particular *Leontopodium alpinum* Cass., which is commonly known under the trivial name "edelweiss". According to another nomenclature "edelweiss" may also be known under the scientific term "*Leontopodium nivale* subsp. *alpinum* (Cass.) Greuter". However, the terms "*Leontopodium alpinum* Cass" and "*Leontopodium nivale* subsp. *alpinum* (Cass.) Greuter" refer to the same plant species and merely reflect a regrouping of the species in botanical nomenclature. Accordingly, the these terms can be used interchangeably in context of the present invention and any definitions and explanations given herein in respect of *Leontopodium alpinum* Cass. also applies to *Leontopodium nivale* subsp. *alpinum* (Cass.) Greuter, mutatis mutandis, and vice versa.

Of course, it is envisaged herein that the compounds to be used according to the present invention may be obtained from other *Leontopodium* species, including but not limited to commercial cultivars, such as *Leontopodium* hybrids. Accordingly the compounds may be obtained from the following, exemplary *Leontopodium* species and cultivars: *L. catipes* (DC.) F. Muell., *L. gnaphalioides* Hieron., *L. japonicum* var. *sandwicense* H. Lév., *L. linearifolium* Britton, *L. meredithae* (F. Muell.) F. Muell., *L. albogriseum* Hand.-Mazz., *L. aloysiodorum* Hort. ex Hand.-Mazz., *L. alpinum* Cass., *L. alpinum* Colm. ex Wink. & Lange, *L. alpinum* Cass. subsp. *nivale* (Ten.) Tutin, *L. amrheinii* Hort. ex Mailers, *L. andersonii* C. B. Clarke, *L. antennarioides* Socz., *L. arbuscula* Beauverd, *L. artemisiifolium* Beauverd, *L. aurantiacum* Hand.-Mazz., *L. beerianum* Beauverd ex Murr, *L. blagoveshczenskyi* Vorosch., *L. bonatii* Beauverd, *L. brachyactis* Gand., *L. caespitosum* Beauverd, *L. caespitosum* Diels, *L. calocephalum* Beauverd, *L. campestre* Hand.-Mazz., *L. catipes* F. Muell., *L. chamaejasme* Beauverd, *L. charkeviczii* V. Yu. Barkalov, *L. chuii* Hand.-Mazz., *L. conglobatum* Hand.-Mazz., *L. coreanum* Nakai, *L. dedekensi* Beauverd, *L. delavayanum* Hand.-Mazz., *L. discolor* Beauverd, *L. dubium* Beauverd, *L. evax* Beauverd, *L. fangingense* Ling, *L. fauriei* Hand.-Mazz., *L. fedtschenkoanum* Beauverd, *L. fimbrilligerum* J. R. Drumm., *L. fischerianum* Beauverd, *L. foliosum* Beauverd, *L. forrestianum* Hand.-Mazz., *L. francheti* Beauverd, *L. futtereri* Diels, *L. giraldii* Diels, *L. gnaphalioides* Hieron. ex Sod., *L. gracile* Hand.-Mazz., *L. haastioides* Hand.-Mazz., *L. hallaisanense* Hand.-Mazz., *L. haplophylloides* Hand.-Mazz., *L. hastatum* Beavera, *L. hayachinense* (Takeda) Hara & Kitam., *L. helveticum* D. Don ex G. Don, *L. himalayanum* DC., *Leontopodium*×*intermedium* Sunderm., *L. jacotianum* Beauverd, *L. jacotianum* Beauverd var. *haastioides* (Hand.-Mazz.) R. C. Srivastava, *L. jamesonii* Beauverd, *L. japonicum* Miq., *L. japonicum* Miq. f. *happoense* Hid. Takah. ex T. Shimizu, *L. javanicum* Zoll. & Mar., *L. junpeianum* Kitam., *L. kamtschaticum* Komarov, *L. krasense* Derganc, *L. kurilense* Takeda, *L. leiolepis* Nakai, *L. leiolepis* Nakai var. *crinulosum* H. S. Pak, *L. leiolepis* Nakai var. *curvicollum* H. S. Pak, *L. leontopodinum* Hand.-Mazz., *L. leontopodioides* Beauverd, *L. leontopodium* Karst., *Leontopodium*×*lindavicum* Sunderm., *L. linearifolium* Britton, *L. linearifolium* Benth. & Hook. f, *L. linearifolium* Hand.-Mazz., *L. longifolium* Ling, *Leontopodium*×*macranthum* Sunderm., *L. maireanum* Beauverd ex Hand.-Mazz., *L. makianum* Kitam., *L. mariae* Muell., *L. melanolepis* Ling, *L. meredithae* F. Muell., *L. micranthum* Ling, *L. microcephalum* (Hand.-Mazz.) Ling, *L. microphyllum* Hayata. *L. monocephalum* Edgew., *L. monoicum* Benth. & Hook. f., *L. montisganeshii* S. Akiyama., *L. muscoides* Hand.-Mazz., *L. nanum* Hand.-Mazz., *L. nivale* (Ten.) Huet ex. Hand.-Mazz., *L. nivale* (Ten.) Huet ex. Hand.-Mazz. subsp. *alpinum* (Cass.) Greuter, *L. niveum* Hand.-Mazz., *L. nobile* Beauverd, *L. ochroleucum* Beauverd, *L. ochroleucum* Beauverd subsp. *campestre* (Ledeb.) V. M. Khanminchun, *L. ochroleucum* Beauverd subsp. *campestre* (Hand.-Mazz.) Khanm., *L. ochroleucum* Beauverd subsp. *conglobatum* (Turcz.) V. M. Kbariminchun, *L. ochroleucum* Beauverd subsp. *conglobatum* (Hand.-Mazz.) Khanm., *L. omeiense* Ling, *L. palibinianum* Beauverd, *L. paradoxum* J. R. Drumm., *L. perniveum* Honda, *L. pirinicum* Hand.-Mazz., *L pulchellum* Beauverd, *L. pusillum* Hand.-Mazz., *L. roseum* Hand.-Mazz., *L rosmarinoides* Hand.-Mazz., *L. sachalinense* Miyabe & Kudo, *L. sandwicense* Rock, *L. shinanense* Kitam., *L. sibiricum* Cass., *L. sinense* Hemsl. ex Forb. & Hemsl., *L. smithianum* Hand.-Mazz., *L. souliei* Beauverd, *L. spathulatum* Kitam., *L. stellatum* A. P. Khokhr., *L. stoechas* Hand.-Mazz., *L. stal-*

*oniferum* Hand.-Mazz., *L. stracheyi* C. B. Clarke ex Hemsl., *L. subulatum* Beauverd, *L. suffruticosum* Y. L. Chen, *L. tataricum* Koran., *L. thomsonianum* Beauverd, *L. umbellatum* Bluff. & Fingerh., *L. villosulum* A. P. Khokhr., *L. villosum* Hand.-Mazz., and *L. wilsonii* Beauverd.

Of course, the compounds provided herein may also be obtained from corresponding cell culture, cell suspension culture or a comparable in vitro cultivation technique, such as callus culture and the like. A person skilled in the art will be aware of corresponding means and methods for establishing and maintaining corresponding cultures. In a preferred embodiment of the invention, the cell culture is derived from roots of *Leontopodium* species described herein above, in particular *Leontopodium alpinum* (edelweiss). Most preferably, the cell culture is derived from hairy roots.

Based on his general knowledge and the teaching provided herein a skilled person is readily in the position to obtain the compounds to be used herein, in particular leoligin, from *Leontopodium* species. Generally, the person skilled in the art is capable of preparing an extract from plants belonging to the genus *Leontopodium* by standard techniques. A preferred method for extracting these compounds from the roots of *Leontopodium alpinum* is provided in Example 1 herein below. An artisan will be aware how to adapt this protocol for extracting the compounds from further *Leontopodium* species and in particular from roots of these plants. A skilled person will also be aware of alternative protocols to be used in this context. The term extract is well known in the art and used accordingly herein. For example, this term may refer to preparations of fluid consistence (fluid extracts and tinctures), semisolid consistence (viscous extracts, syrup concentrate) or solid consistence (dried extracts), which are usually prepared using fresh or dried plant material.

The extract obtained from *Leontopodium* species is an extract that is received by the use of an organic or non-organic solvent. Suitable solvents are hexane, heptane, petroleum benzene, acetone, chloroform, dichloromethane, ethyl acetate, diethylether, liquid carbon dioxide, ethanol, ternary butyl methyl ether (tBMe) and mixtures of water and alcohol. The extract may be obtained by extracting the plant material, in particular roots, with any of the solvents separately. It is further possible to subsequently extract the obtained extract with a second solvent or mixtures of different solvents. An exemplary, non-limiting solvent to be used in a first extraction step is hexane. However, any of the above solvents can be used in such a first extraction step. This first extraction step may be followed by (a) subsequent second (or further) extraction step with at least one of the above exemplary solvents, e.g. dichloromethane, chloroform or ternary butyl methyl ether (tBMe). Extraction of the compounds disclosed herein (in particular compounds of formula (I), such as leoligin and/or its (di)methoxy-derivative(s)) in accordance with the present invention is also illustrated in the appended examples. Preferably, dichloromethane and methanol are used as extraction solvents. In subsequent extraction, it is preferred that the compounds are first extracted with n-hexane, followed by a subsequent extraction with dichloromethane, chloroform or tBMe. As shown herein, the lignan content (i.e. content of compounds of formula (I), such as leoligin and/or its (di) methoxy-derivative(s)) can be increased by a second or further extracting steps using the herein described methods, and in particular the above solvents. Also the use of chromatographic methods, such as Sephadex-LH20-column chromatography and in particular silica gel column chromatograph is advantageous in this context. As also demonstrated in the appended examples, an increase in the leoligin content from about 0.7% to about 2.2% can be achieved using Sephadex-LH20-column chromatography. It is shown herein that a pronounced increase in the leoligin content from about 1.4% to about 10% can be achieved using silica gel chromatograph.

It is envisaged herein that further chromatographic methods to increase the content of the herein disclosed compounds (in particular compounds of formula (I), such as leoligin and/or its (di)methoxy-derivative(s)) can used in addition or in the alternative to the above described methods. Exemplary, non-limiting chromatographic methods to be used in this context are reversed phase column chromatography or (semi)-preparative HPLC using water/acetonitrile mixtures or comparable solvent mixtures known in the art. Alternatively, techniques of liquid-liquid extractions (discontinuous or continuous methods) can be used to increase the content of the herein disclosed compounds (in particular compounds of formula (I), such as leoligin and its (di)methoxy-derivative(s)). An exemplary liquid-liquid extraction is high speed counter current chromatography using a solvent system of two not mixable solvents.

The preparation of the basic extract of *Leontopodium* species, in particular *Leontopodium alpinum*, may comprise mechanical pulping. sonication, use of mortars and pestles, freeze-thawing cycles, use of blenders (like Waring-Blenders, Polytron), liquid homogenization and maceration (see also appended examples), or e.g. Dounce homogenization, Potter-Elvehjem, French Press etc. In the appended examples, a mechanical maceration is used. However, the extracts may be obtained by disrupting the cells and cells from the *Leontopodium* species by any mechanical/physical or chemical means, like by use of detergents.

Mechanical methods rely on the use of rotating blades to grind and disperse large amounts of complex tissue, such as plant leaves, flowers, seeds and in particular roots. The Waring blender and the Polytron are commonly used for this purpose. Unlike the Waring blender, which is similar to a standard household blender, the Polytron draws tissue into a long shaft containing rotating blades.

Liquid-based homogenization is the most widely used cell disruption technique for cultured cells. Cells are lyzed by forcing the cell or tissue suspension through a narrow space, thereby shearing the cell membranes. Three different types of homogenizers are in common use. A Dounce homogenizer consists of a round glass pestle that is manually driven into a glass tube. A Potter-Elvehjem homogenizer consists of a manually or mechanically driven Teflon pestle shaped to fit a rounded or conical vessel. The number of strokes and the speed at which the strokes are administered influences the effectiveness of Dounce and Potter-Elvehjem homogenization methods. Both homogenizers can be obtained in a variety of sizes to accommodate a range of volumes. A French press consists of a piston that is used to apply high pressure to a sample volume of 40 to 250 ml, forcing it through a tiny hole in the press. Only two passes are required for efficient lysis due to the high pressures used with this process. It is of note that in more industrial applications also other, larger devices may be employed to prepare the extracts from *Leontopodium* species.

Sonication is also a physical disruption commonly used to break open cells. The method uses pulsed, high frequency sound waves to agitate and lyse cells and finely diced tissue. To prevent excessive heating, ultrasonic treatment may be applied in multiple short bursts to a sample immersed in an ice bath. Sonication is best suited for volumes <100 ml.

The freeze/thaw method is commonly used to lyse bacterial and cells from higher organism. The technique involves freezing a cell suspension in a dry ice/ethanol bath or freezer and then thawing the material at room temperature or 37° C.

This method of lysis causes cells to swell and ultimately break as ice crystals form during the freezing process and then contract during thawing. Multiple cycles are necessary for efficient lysis, and the process can be quite lengthy. Cells, organisms as well as tissue might be treated with various agents to aid the disruption process. Chemical substances, such as hexane, petroleum benzene, chloroform, dichloromethane, acetone, ethyl acetate, diethyl ether, ethanol and mixtures of water and alcohol or mixtures of different solvents may be added during or before mechanical disruption. Lysis can also be promoted by suspending cells in a hypotonic buffer, which cause them to swell and burst more readily under physical shearing. Processing can be expedited by treating cells with glass beads in order to facilitate the crushing of cell walls. Viscosity of a sample typically increases during lysis due to the release of nucleic acid material. DNase may be added to samples along with to reduce this problem.

Less preferred, however envisaged, is the use of detergents in the preparation of the extracts to be treated in accordance with the present invention. Detergents are a class of molecules whose unique properties enable manipulation (disruption or formation) of hydrophobic-hydrophilic interactions among molecules in biological samples. Such detergents may be used to lyse cells, solubilize membrane proteins and lipids. Generally, moderate concentrations of mild (i.e., nonionic) detergents compromise the integrity of cell membranes, thereby facilitating lysis of cells and extraction of soluble protein, often in native form. Using other conditions, detergents effectively penetrate between the membrane bilayers at concentrations sufficient to form mixed micelles with isolated phospholipids. Detergents may be, e.g. Triton X-100®, Triton-X-114®, NP-40®; CHAPS, Tween-20®, Tween-40®), Tween-80®, Octyl Glucoside, Octylthio Glucoside, Brij-35, Brij-58, SDS and the like. However, it may be useful to stabilize the extract by certain chemical means. Illustrative stabilizers are discussed herein below in context of pharmaceutical or cosmetic compositions.

The cells and plants to be employed in order to obtain the basic extract may be cells of natural origin as well as cultured cells or plants. It is preferred herein that the cells or plants and in particular roots of the plants are dried before mechanical disruption/maceration as described. herein above. The cells or plants may be air dried, lyophilized (freeze-dried) or, though less preferred, dried in an oven. It is preferred herein that the "cell(s)" and "plant(s)" to be used as a basic material are fresh, i.e. harvested shortly before the extract is prepared. Nonetheless, it is possible to store the basic material before its use in the preparation of the extract. For example, the basic material may be lyophilized (freeze-dried) or simply frozen and stored at low temperatures, e.g. at about $-20$ to $-30°$ C. or as low as $-80°$ C.

In context of the present invention, the term "cell" and "plant" to be used as basic material for preparing the extract to be treated by the method of the present invention also comprises the use of "tissues". Such tissues may be leaves, sprouts, or reproductive organs e.g. flowers. Preferably, the tissues are roots, in particular hairy roots. In addition, callus or cell cultures may be used which may be derived from tissues described above, in particular roots, and which are grown in liquid culture or on solidified culture medium. The appropriate culturing methods of calli or cell cultures are known to a person skilled in the art. A culture medium may be for example a MS (Murashige and Skoog) medium while a solidifying agent may be agarose, plant agar or bacto agar. A basic culture medium such as a MS medium may be modified in respect to pH range, carbon or nitrogen source, amino acids or vitamins amongst others. The use of plants regenerated from such callus or cell culture is also envisaged, as well as plants or organisms generally grown or propagated in vitro.

Methods for preparing the extract are known in the art and also described herein. Preferably, the extract is further processed shortly after its preparation (e.g. the extract is used in the preparation of a herein disclosed pharmaceutical composition); however, it is also possible to store the extract for some time before they are used in accordance with the present invention. The extracts may, for example, be stored in lyophilized form or in form of dried extracts. However, each storage form known in the art is be employed, as long as the storage has the effect that the extract (and its components) remain efficacious over a long time period, i.e. the stored extract has, preferably, substantially the same efficacy as the fresh extract.

Dried extracts can be routinely prepared by methods known in the art. For example, following mechanical disruption of the basic (plant) material by e.g. maceration or percolation, the material can be extracted using (a) solvent(s) or mixtures thereof as described herein. After separation of the fluid phase and the extract residue (which contains e.g. cellulose. pectin and the like and which does, preferably, not contain the active substance(s) as disclosed herein, i.e. predominantly leoligin and its ((di)methoxy)-derivative(s). The fluid extract (i.e. the fluid phase of the obtained extract) may be concentrated taking advantage of routine techniques, some of which are exemplarily described herein below. Such concentration techniques include, but are not limited to fluidised-bed drying, concentration to a syrup or concentrated fluid extract, spray drying, freeze drying or the use of a vacuum dryer, a drying tunnel, vacuum band dryer or a drying hurdle. Often organic-hydrous fluid extracts (such as the fluid extract obtained herein using an organic solvent) are concentrated by nucleate boiling or surface evaporation.

Routine drying techniques employed in the pharmaceutical field comprise distillation and drying under normal conditions (i.e. room temperature) also methods which take advantage of variations in pressure and temperature in order to obtain the dried extracts. One well known method for preparing a dried extract is as follows: First, a fluid extract or tincture is prepared; after subsequent distillation of the solvent a viscous extract is obtained, to which often adjuvants and/or excipients (e.g. lactose, polyvinylpyrrolidone, sucrose, silicon dioxide and the like are added. This moist mass is then dried in suitable driers. Also employed in this context is the use of a vacuum band dryer (Mitchell Dryers Ltd), wherein a dried extract is obtained from the viscous extract after a pre-drying step using downdraft vaporizers.

Also envisaged herein is the use of commercially available extracts, in particular dried extracts, obtained from (a) plant(s) belonging to the genus *Leontopodium*.

After mechanical disruption of the cell(s), tissue(s) or whole plant(s) the plant material may be further macerated and/or dissolved/suspended in an organic solvent, such as hexane, petroleum benzene, chloroform, dichloromethane, acetone, ethyl acetate, diethyl ether, liquid carbon dioxide, ethanol and mixtures of water and alcohol with any of the solvents separately or subsequently with a second solvent or mixtures of different solvents. Preferably, dichloromethane and methanol are used as extraction solvents.

As shown in the appended examples, a hexane extract comprising 0.67% leoligin and 1.47% leoligin and its methoxy-derivative(s) can easily be prepared by routine techniques. However, it is preferred herein that the extract is enriched in the compounds described and provided herein, in particular compounds of formula (I), such as leoligin and/or its ((di)methoxy) derivative(s). As also shown in the appended examples, higher yields (relative to the leoligin content [w/w %] in the extract) typically in a range between 0.7% to 1.5% can easily be obtained using standard extraction methods and solvents (such as dichloromethane). Using these standard extraction methods. yields of up to about 2.2% of leoligin and its 5-methoxy-derivative can be obtained. As described herein, the content of compounds of formula (I), in particular leoligin (and/or its (di)methoxy-derivative(s)), can be further increased by multiple extraction rounds, e.g. a first extraction step using hexane followed by (a) subsequent extraction step(s) using e.g. dichloromethane, chloroform or ternary butyl methyl ether (=tBMe). A total lignan content (predominantly compounds of formula (I), in particular leoligin and/or its (di)methoxy-derivative(s)) of at least 2.4% can be achieved if subsequent extraction steps are applied The concentration of lignans (predominantly compounds of formula (I), in particular leoligin and/or its (di)methoxy-derivative(s)) can also be increased by the use of Sephadex-LH20-column chromatography (increase in the leoligin content from about 0.7% to about 2.2%).

Preferably, the extract is an enriched extract, i.e. contains leoligin and its ((di)methoxy)-derivative(s) in a high amount. Such an enriched extract can, for example, be obtained by taking advantage of silica gel chromatography as demonstrated in the appended examples. Silica gel column chromatography is well known in the art and described in detail in standard textbooks, such as "Preparative Chromatography Techniques" by Hostettmann, K. Marston, Andrew Hostettmann, Maryse, Springer-Verlag GmbH, 2007, 260 p. In the experimental section, it was shown that a pronounced increase in the leoligin content from 1.36% to 9.76% [w/w] can be achieved using silica gel chromatograph (mobile phase: petroleum ether-acetone).

Accordingly, it is preferred herein that the solid components of the extract (e.g. after evaporating the solvent by any of the drying methods described herein) comprise at least 0.05%, 0.1%, 0.5%, 0.7%, 1%, 1.5%, 2.0%, 2.5% or 3.0% of the compounds of formula (I), in particular leoligin. and/or ((di)methoxy)-derivative(s) thereof, wherein an extract the solid components of which comprise at least 0.7% of these compounds can be considered an "enriched" extract in context of the present invention. More preferably, the solid components of the extract comprise at least 5%, 6%, 7%, 8%, and most preferably at least 9% or 10% of the compounds of formula (I), in particular leoligin and/or ((di)methoxy)-derivative(s) thereof. An extract, the solid components of which comprise at least 9% of these compounds can be considered a "highly enriched" extract. An "enriched extract", and, in particular a "highly enriched" extract as defined herein, represents therefore a preferred embodiment of the present. "Enriched" or "highly enriched" extracts are particularly useful in the herein disclosed medical context, in particular the treatment, prevention, or amelioration of (a) hyperplastic disorder(s) as defined herein. In accordance with the present invention, it is also preferred herein that the solid components of the (highly enriched) extract comprise at least 15%. 20%, 25%, 30%, 40%. 50%, 60%. 80% or 90% of the compounds of formula (I), in particular leoligin and/or (a) derivative(s) thereof (preferably (a) (di)methoxy-derivative(s), more preferably the herein disclosed derivatives 5-Methoxy-Leoligin and/or 5,5'-Dimethoxy-leoligin). Based on the teaching provided herein a skilled person is readily in the position to determine whether an extract prepared in accordance with the present invention is enriched/highly enriched in compounds of formula (I), in particular leoligin and/or (a) derivative(s) (preferably (a) (di)methoxy-derivative(s), more preferably the herein disclosed derivatives 5-Methoxy-Leoligin and/or 5,5'-Dimethoxy-Leoligin). Most preferably, pure compounds of formula (I) are obtained, i.e. solid components of the extract comprise at least 95% of the compounds described and provided herein. In order to obtain a higher yield of the compounds of formula (I), the basic extracted material may be subjected to at least one further and up to eight further cycles of extraction. It is preferred that the (enriched/highly enriched) extract is obtained from (a) plant(s) belonging to the genus *Leontopodium*, in particular from the roots of such (a) plant(s). Exemplary species or cultivars of the above genus and to be used in accordance with the present invention are known in the art and also disclosed herein.

It is envisaged herein, that the "enriched/highly enriched" extract comprises predominantly leoligin as active substance, in particular in combination with its methoxy-derivatives. Based on the teaching given herein, a skilled person is readily in the position to determine which amount of the (enriched/highly enriched) extract is to be employed in particular in the preparation of the pharmaceutical compositions comprising/consisting of the extract depending on the concentration/content of the herein disclosed active substance (preferably of leoligin and/or its (di)methoxy-derivative(s) and mixtures thereof). Preferably, the extract employed/contained in the pharmaceutical composition exerts substantially the same medical effect as a pharmaceutical composition comprising (a) compound(s) of formula (I), in particular leoligin and/or its (di)methoxy-derivative(s) (or mixtures thereof), more particularly leoligin or the (di)methoxy-derivative alone (as shown in the appended examples). "Substantially the same effect" means in context of the present invention that the "effect" varies by less than 10%, preferably less than 5%, most preferably less than 1%. An exemplary "effect" to be measured is inhibition of vascular smooth muscle cell (SMC) proliferation which is a central mechanism underlying hyperplastic diseases/disorders as described herein above and also demonstrated in the appended examples.

As mentioned above, the herein provided and disclosed extracts obtained from (a) plant(s) belonging to the genus *Leontopodium* can, in accordance with the present invention, be used in a medical context. Accordingly, the present invention relates in one embodiment to a pharmaceutical composition comprising a root extract obtained from a plant belonging to the genus *Leontopodium*. A further embodiment relates to a pharmaceutical composition comprising an extract obtained from a plant belonging to the genus *Leontopodium*, whereby the extract is highly in enriched in the herein disclosed compounds, in particular compounds of formula (I), such as leoligin and/or its (di)methoxy-derivative(s) (or mixtures thereof). It is preferred herein that the highly enriched extract predominantly comprises leoligin and/or its (di)methoxy-derivative(s) (or mixtures thereof). Formulas of leoligin and preferred (di)methoxy-derivatives thereof are also provided herein. The herein disclosed pharmaceutical composition comprising a (root) extract obtained from a plant belonging to the genus *Leontopodium*, wherein the extract is preferably enriched (most preferably highly enriched) in the compounds of formula (I), in particular leoligin and/or ((di)(methoxy-))derivatives thereof, is used in the treatment, prevention or amelioration of a hyperplastic disorder as defined herein. The term "root extract" used herein means an extract obtained from roots, i.e. plant material from the lower parts of the plants are used, preferably only roots are used as raw plant material in the preparation of the extract. It is preferred in this context that the pharmaceutical composition consists of the (preferably enriched, more preferably highly enriched) extract. However, further excipients/adjuvants/carriers and the like as described herein and known in the art may be contained in the pharmaceutical composition in addition to the extract. In accordance with the above, a composition comprising (consisting of) a(n) (root) extract obtained from a plant belonging to the genus *Leontopodium*, whereby the extract is (highly) in enriched in compounds of formula (I), in particular leoligin and/or its (di)methoxy-derivative(s) (or mixtures thereof), is provided herein for use in medicine or for use as a medicament. Also a (root) extract obtained from a plant belonging to the genus *Leontopodium*, whereby the extract is (highly) in enriched in compounds of formula (I), in particular leoligin and/or its (di)methoxy-derivative(s) (or mixtures thereof), for use in medicine or as a medicament is provided. It is envisaged that the above (pharmaceutical) compositions/extracts are to be used in accordance with the present invention in the treatment, prevention or amelioration of a hyperplastic disorder as disclosed and defined herein.

In order to obtain the single compounds, the extracts may be prepared and evaporated as described above and, submitted to further purification by column chromatography using silica gel, silica gel modified by means of $AgNO_3$, reversed phase material (RP18) or Sephadex LH 20® as stationary phases. Additionally, other separation techniques e.g. high speed counter current chromatography or (semi)-preparative HPLC might be used as well. Fractions obtained by the above mentioned chromatographic techniques may be further purified, e.g. by another cycle of chromatographic purification. For example. a cross-linked dextran gel may be used for such further purification, like e.g. Sephadex LH-20®. This kind of chromatography is usually performed in the presence of an organic solvent such as methanol, acetone dichloromethane and the like. It is envisaged herein that the herein described pharmaceutical compositions comprising the extract disclosed herein may also (in addition) comprise the pure (and/or (substantially) purified, e.g. purified from the extract) active substances (i.e. compound of formula (I), in particular Leoligin and/or its (di)methoxy derivative(s)). In accordance with the above, it is preferred herein that the pharmaceutical composition comprises essentially the plant extracts disclosed herein and obtained by the herein described methods. Also envisaged herein is a pharmaceutical composition, which does not comprise the herein described extract, but comprises the pure (and/or (substantially) purified, e.g. purified from the extract) active substances (i.e. compound(s) of formula (I), in particular Leoligin and/or its (di)methoxy-derivative(s)). The extract can also be obtained by alternative extraction methods known in the art e.g. supercritical carbon dioxide extraction, percolation or Soxhlet-extraction and adaptable for the means and methods of the present invention by one skilled in the art.

Also envisaged herein, though less preferred, the compounds may also be obtained from upper parts of the plants, e.g. flowers, stems, leaves, seeds and the like. *Leontopodium alpinum* (Edelweiss) plants to be extracted are easily available e.g. from the Station féderale de recherches en production végetals de Changins (see also http://www.admin.ch/sar/rac; Revue Suisse Vitic. Arboric. Horde. 31(2), 889-96 (1999)).

Figure 8:
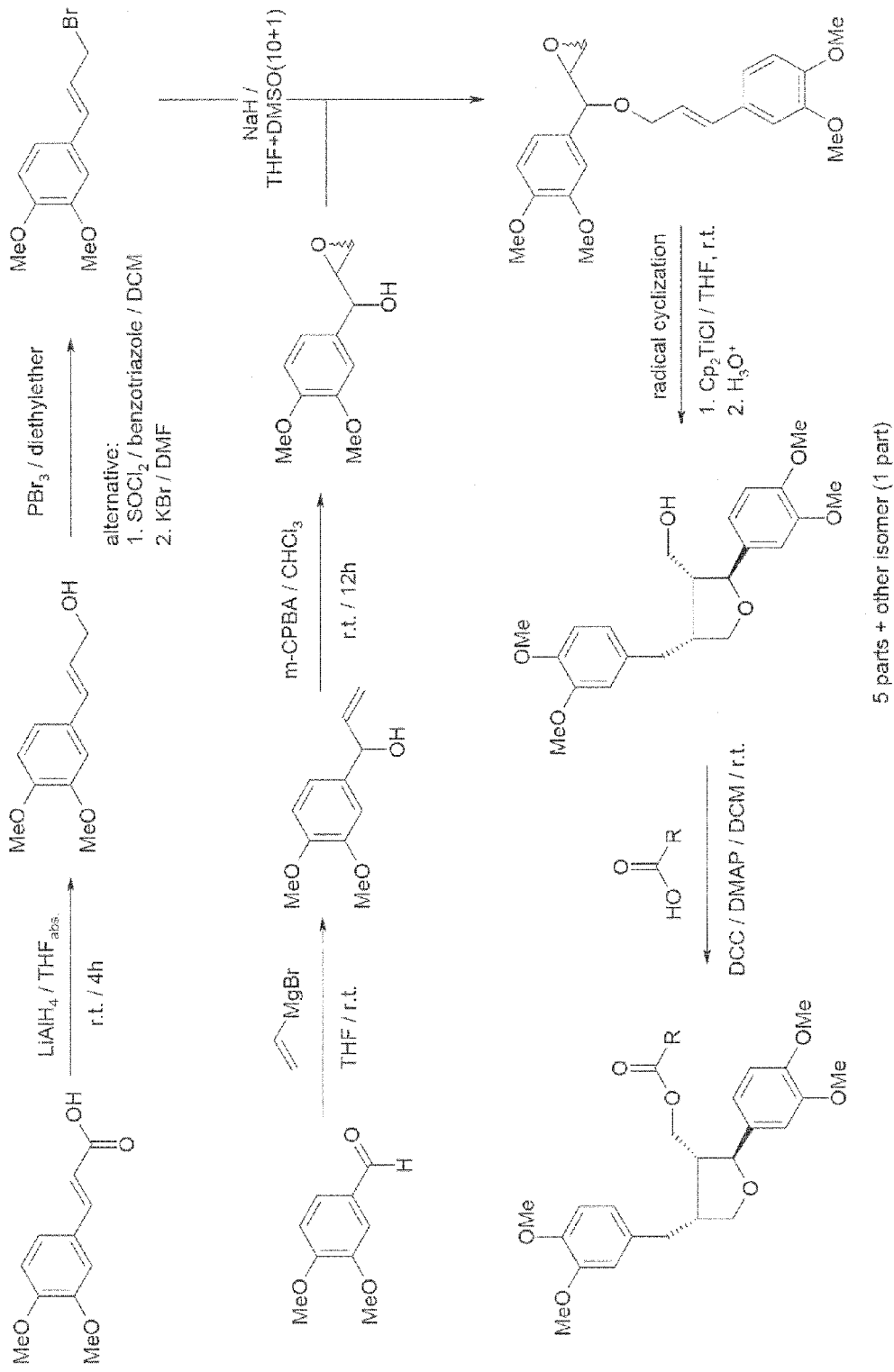

In an alternative embodiment, the compounds to be used herein may also be synthesized. An exemplary synthetic pathway of leoligin is shown in FIG. 8. The shown synthetic pathway might be adapted by a change of the corresponding educts to obtain other compounds of the present invention A skilled person will be aware of methods of synthesizing the compounds of the present invention, in particular leoligin, or may deduce corresponding methods e.g. from Li Hong Hu, J. Nat. Prod. 68, 342-8. (2005); Babasaheb P. Bandgar, Monat-shefte für Chemie 135, 1251-5 (2004); J Pijus Kumar Mandal, Org. Chem. 63, 2829-34 (1998); Subhas Chandra Roy, J. Org. Chem. 67, 3242-8 (2002).

As mentioned above, the active compounds referred to herein may also be provided via semi-synthetic methods, e.g. by derivatizing a natural product such as leoligin. Suitable derivatization reactions known in the art comprise methods wherein the ester bond present in leoligin is saponified to produce an alcohol. The alcohol may be oxidized to provide a carbonyl/carboxylic acid functionality to be reacted with an alcohol, thiol or amine, or it may be esterified with a different organic acid, it may be converted into an amine etc.

The pharmaceutical composition may comprise the compounds provided in the present invention. The compounds to be used in accordance with the present invention may be obtained from *Leontopodium* plants as described herein above and/or chemically synthesized.

The pharmaceutical composition of the present invention comprising compounds of formula (I) and, in particular, leoligin, will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations.

The skilled person knows that the effective amount of pharmaceutical composition administered to an individual will, inter alia, depend on the nature of the compound. For example, if said compound is a lignan the total pharmaceutically effective amount of pharmaceutical composition administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day. If given continuously, the pharmaceutical composition is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect. The particular amounts may be determined by conventional tests which are well known to the person skilled in the art.

Pharmaceutical compositions of the invention may be administered orally, rectally, parenterally, intracisternally, intravaginally, intraperitoneally, topically (as by powders, ointments, drops or transdermal patch), bucally, or as an oral or nasal spray. Accordingly, also the compound provided herein may be administered by any one of a parenteral route, oral route, intravenous route, intraarterial route, intramuscular route, intracardial route, intrapulmonal route, intravesical route, intravitreal route, subcutaneous route, intranasal route or transdermal route.

Pharmaceutical compositions of the invention preferably comprise a pharmaceutically acceptable carrier. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained release pharmaceutical composition also include liposomally entrapped compound. Liposomes containing the pharmaceutical composition are prepared by methods known per se: DE 3.218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

In one embodiment, a compound as defined herein above is for use in treating, preventing or ameliorating of a hyperplastic disease/disorder. The present invention also relates to the use of a compound as defined herein for the preparation of a pharmaceutical composition for the treatment, prevention or amelioration of a hyperplastic disease/disorder. Hyperplasia/Hyperplastic diseases/disorders (malign and benign) are characterised by abnormal (i.e. hyperphysiological) high numbers of cell divisions in an organ or tissue. Hyperplasia may be a pathological or a physiological process which is however always clearly distinguishable from hypertrophy. Hypertrophy is the enlargement of tissue or an organ by enlargement of single cells. Hyperplasia is the physiologic or pathological enlargement of tissues or organs due to an increase in the number of cells due to cell division. An important part of vein graft disease is a process called intimal hyperplasia, being a hyperplastic process, which leads to narrowing of the vessel lumen and graft failure. Another process that contributes to vein graft disease is atherosclerosis, which is characterised by deposition of lipids in the vessel wall, infiltration of macrophages, foam cell formation and fatty streak formation, tissue remodelling which is associated with the proliferation and infiltration of the intima by smooth muscle cells, deposition of extracellular matrix, and plaque formation. In addition, inflammatory processes crucially contribute to atherosclerosis, vein graft disease and hyperplasia. These processes may lead to plaque rupture which may lead to the thrombosis and or occlusion of the vein graft. In the process of atherosclerosis proliferation of smooth muscle cells plays an important role, also this proliferation is a hyperplastic process.

A preferred hyperplastic disease to be treated, prevented or ameliorated in accordance with the present invention is intimal hyperplasia and/or vein graft disease. Vein graft disease is characterised by intimal hyperplasia i.e. the abnormally increased proliferation of smooth muscle cells in the intima and media of the vessel wall. Preferably, the hyperplastic disease/disorder is hyperplasia. The hyperplasia may be intimal hyperplasia. In a preferred embodiment the intimal hyperplasia is stenosis or restenosis. The intimal hyperplasia may also be atherosclerosis. The meaning of the terms "hyperplasia", "intimal hyperplasia", "stenosis", "restenosis" and "atherosclerosis" is well known in the art and may be deduced from standard textbooks such as "Handbook of Coronary Stents" edited by P. W. Serruys and B. Rensing, 4th edition, published by Taylor&Francis, or from the "Handbook of Drug-eluting stents, edited by P. W. Serruys and A. H. Gershlick, published by Informa Healthcare. It is particularly envisaged herein that vein graft diseases may be treated in accordance with the present invention.

The hyperplastic disease may also be a proliferative or neoplastic disease. A proliferative disease is generally considered as a disease associated with uncontrolled/increased proliferation of cells. Neoplasia or neoplastic diseases are characterised by the new formation of tissues either as a physiological process or as a pathological process. Typical pathological neoplastic diseases are tumors/cancers. Non-limiting examples of proliferative diseases are benign proliferative diseases, such as benign proliferative breast disease, cancerous disorders, like blood tumors, leukemia, as well as solid tumors like B-cell lymphomas, myelotic cancer, prostate cancer, breast cancer, colon cancer, lung cancer and skin cancer.

In one embodiment, the present invention relates to a method for treating, preventing or ameliorating a hyperplastic disease/disorder comprising the administration of a compound as defined herein to a subject in need of such a treatment, prevention or amelioration. It is preferred that the subject is a human.

A preferred application form is a drug eluting stent system described herein may be a polymer based drug delivering system or a polymer coated drug delivering system. It is to be understood that the compound of formula (I) described and provided herein, and in particular leoligin and/or (a) ((di)methoxy)-derivative(s) thereof, is applied to the drug delivering system in combination with (a) polymer(s). Therefore the drug component (the active ingredient) is embedded in a non-erodible polymer carrier (base coat formulation) which is surrounded by a suitable topcoat layer to control the release of the embedded drug. A possible application form would be a system containing parylene C and the following two non-erodible polymers: polyethylene-co-vinyl acetate (PEVA) and poly n-butyl methacrylate (PBMA). A combination of the two polymers (67%/33%) mixed with the compound of formula (I) described and provided herein, and in particular leoligin and/or (a) ((di)methoxy)-derivative(s) thereof, makes up the basecoat formulation which is applied to a parylene C treated stent. A drug-free topcoat of PBMA polymer is applied to the stent surface to control the release kinetics of the compound of formula (I) described and provided herein, and in particular leoligin and/or (a) ((di)methoxy)-derivative(s) thereof. Alternatively a single layer polymer e.g. a Translute® polymer carrier, might be used as drug delivering matrix. The drug/polymer coating is adhered to the entire surface (i.e., luminal and abluminal) of the stent.

In one embodiment, the present invention relates to a medical device comprising, containing or having been contacted with a compound as described herein, i.e. a compound with formula (I), in particular leoligin.

Preferably, the medical device is a drug delivering system. Such a drug delivering system may, for example, be a balloon catheter. A balloon catheter is a kind of a catheter having an inflatable balloon at its tip. The balloon catheter can be used to widen a narrow opening or passage within the human or animal body, and may be of particular advantage in the treatment of a hyperplastic disease like e.g. intimal hyperplasia, restenosis, stenosis or vein graft disease. In a first step, the deflated balloon catheter is positioned at the side to be widened and is then in a second step inflated. After widening the opening or passage the balloon is deflated and can then easily be removed. It is envisaged that a balloon used in this context may be coated or may contain the compound of formula (I), in particular leoligin and/or its ((di)methoxy)-derivative(s). These compounds may be delivered to the cells or tissue surrounding the balloon during and/or upon insertion, inflation and deflation of the balloon. A balloon as described herein above may be particularly beneficial in this context since it can be completely removed after the widening procedure, reducing the possible occurrence of inflammatory responses.

The drug delivering system described herein may be a polymer based drug delivering system or a polymer coated drug delivering system. It is to be understood that the compound of formula (I) described and provided herein, and in particular leoligin and/or ((di)methoxy)-derivative(s) thereof, is applied to the drug delivering system in combination with (a) polymer(s). Preferably, the drug delivering system provides for a sustained release of the compounds. Non-limiting examples of polymer to be used for coating the drug delivering systems are polyethylene glycol; polystyrene; polyurethane; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

Preferably, the medical device provided herein is a stent. In context of the present invention the term "stent" means a medical device that is inserted into a natural conduit of the body to prevent or counteract a disease-induced localized flow constriction. Stents provided herein may preferably be used in the treatment of (a) hyperplastic disease(s)/disorder(s), in particular (a) vein graft disease(s). The meaning of the term "drug eluting stent" is well known in the art and may, for example, be deduced from the "Handbook of Coronary Stents" edited by P. W. Serruys and B. Reusing, $4^{th}$ edition, published by Taylor&Francis, or from the "Handbook of Drug-eluting stents, edited by P. W. Serruys and A. H. Gershlick, published by Informa Healthcare. Based on his general knowledge and the teaching provided herein and in standard text books, like the above-mentioned Handbook of Coronary Stents, a person skilled in the art is readily in the position to develop and prepare a stent and in particular a drug eluting stent comprising, containing or having been contacted with a compound of formula (I), in particular leoligin and/or its ((di)methoxy)-derivative(s). A skilled person will be aware of methods for coating the stent with the herein described and provided compound, whereby the coating allows delivery of the compound to cells and/or tissue, e.g endothelial cells/endothelium. The stent, in particular the drug eluting stent, to be used herein may also be a biodegradable stent, i.e. the stent is degraded/dissolved some time after insertion of the stent in a passage to be widened as described herein above.

In a preferred embodiment of the present invention, the medical device is used for the delivery of a drug, wherein the drug is the compound provided herein, i.e. the compound of formula (I) and in particular leoligin and/or ((di)methoxy)-derivative(s) thereof. Therapeutic systems which are used in the art as "drug delivering system", in particular as "drug eluting stent" contain the agents Paclitaxel (Taxol®) or Sirolimus which are structurally not related to the compounds to be used in context of the present invention. Further, these agents exhibit their effect in a completely different way compared to the present compounds of formula (I), and in particular, leoligin and/or its ((di)methoxy)-derivative(s).

Paclitaxel promotes the assembly of microtubules from tubulin dimers and stabilizes microtubules by preventing depolymerization. This stability results in the inhibition of the normal dynamic reorganization of the microtubule network that is essential for vital interphase and mitotic cellular functions Premarket Approval Applications (PMA) of the FDA; P030025: TAXUS™ Express 2™ Paclitaxel-Eluting Coronary Stent System (Monorail and Over-the-Wire). Issued Mar. 4, 2004; Part 2—Summary of Safety and Effectiveness Data. http://www.fda.gov/cdrh/pdf3/P030025.html. The mechanism (or mechanisms) by which a CYPHER™ Stent (Sirolimus is the active agent contained therein) exerts its effect on neointima production as seen in clinical studies has not been established. Sirolimus inhibits T-lymphocyte activation and smooth muscle and endothelial cell proliferation in response to cytokine and growth factor stimulation. In cells, sirolimus binds to the immunophilin, FK Binding Protein-12 (FKBP-12). The sirolimus-FKBP-12 complex binds to and inhibits the activation of the mammalian Target of Rapamycin (mTOR), leading to inhibition of cell cycle progression from the GI to the S phase Premarket Approval Applications (PMA) of the FDA; P020026: Cypher sirolimus-eluting coronary stent on the raptor over-the-wire delivery system or raptorrail rapid exchange deliver. Issued Apr. 24, 2003; Part 2—Summary of Safety and Effectiveness Data. http://www-.fda.gov/cdrh/pdf2/P020026.html.

The compound provided herein, such as compounds of formula (I) and in particular leoligin, may also be used in liquids intended for rising and/or storing (a) venous bypass(es), particularly before and/or during bypass operations. The rinsing and/or storage of the venous bypass(es) in such a liquid is particularly advantageous since such a kind of "pretreatment" of the bypass(es) may prevent damage of endothelial cells and/or inhibit the pathological proliferation of smooth muscle cells, and consequently reduce the probability of hyperplastic disease/disorder, in particular intimal hyperplasia, stenosis, restenosis or vein-graft disease.

Accordingly, a rinsing and/or storage solution for a venous bypass is provided herein which comprises the compound of formula (I) and in particular leoligin and/or its ((di)methoxy)-derivative(s). The storage solution may, in addition to the compound described herein, comprise further components, such as stabilizers, preserving agents, buffering agents, salts (like NaCl), osmotically active compounds, proteins (like albumin). It is to be understood that the rinsing and/or storage solution may comprise only one compound of formula (I) or, optionally, different compounds of formula (I), like leoligin and/or different (a) ((di)methoxy)-derivative(s) of leoligin. The rinsing/storage solution may comprise the same molar concentration of these different compounds, or, alternatively, different concentrations. For example a first compound may be present at a double concentration compared to a second compound. Preferably, the molar concentration of the compound in the rinsing/storage solution is between 1 and 500 µM, preferably between 10 and 200 µM preferably 50 µM. It is envisaged herein that the leak tightness of the venous bypass(es) rinsed with or stored in the solution as described herein above is to be tested with a device suitable for such a test. Leak tightness tests of venous bypass(es) are well known in the art and a person skilled in the art is therefore aware of corresponding means and methods to perform such a test.

The compound(s) of formula (I) may also be applied periadventially to (a) venous bypass(es) before, during and/or after a bypass operation, whereby the compound(s) may, optionally, be applied with a gel (e.g. Pluronic gel) or without a gel.

The present invention also relates to a method for rinsing and/or storing a venous bypass comprising contacting the venous bypass with the compound of formula (I), in particular leoligin and/or (a) ((di)methoxy)-derivative(s) thereof.

The present invention is further described by reference to the following non-limiting figures and examples.

The Figures show:

FIG. 1. Leoligin is a constituent of Edelweiss (*Leontopodium alpinum* Cass.) roots Edelweiss is one of the most popular alpine plants and is also used in folk medicine for the treatment of indigestion, fever, and "abdominal aches". FIG. 1A shows the flower of Edelweiss (*Leontopodium alpinum* Cass.). FIG. 1B shows the chemical structure of leoligin—IUPAC name: [(2S,3R,4R)-4-(3,4.-dimethoxybenzyl)-2-(3,4-dimethoxyphenyl)tetrahydrofuran-3-yl]methyl (2Z)-2-methylbut-2-enoat. Leoligin is a lignan, which was isolated from the roots of Edelweiss (*Leontopodium alpinum* Cass.).

Figure 2:
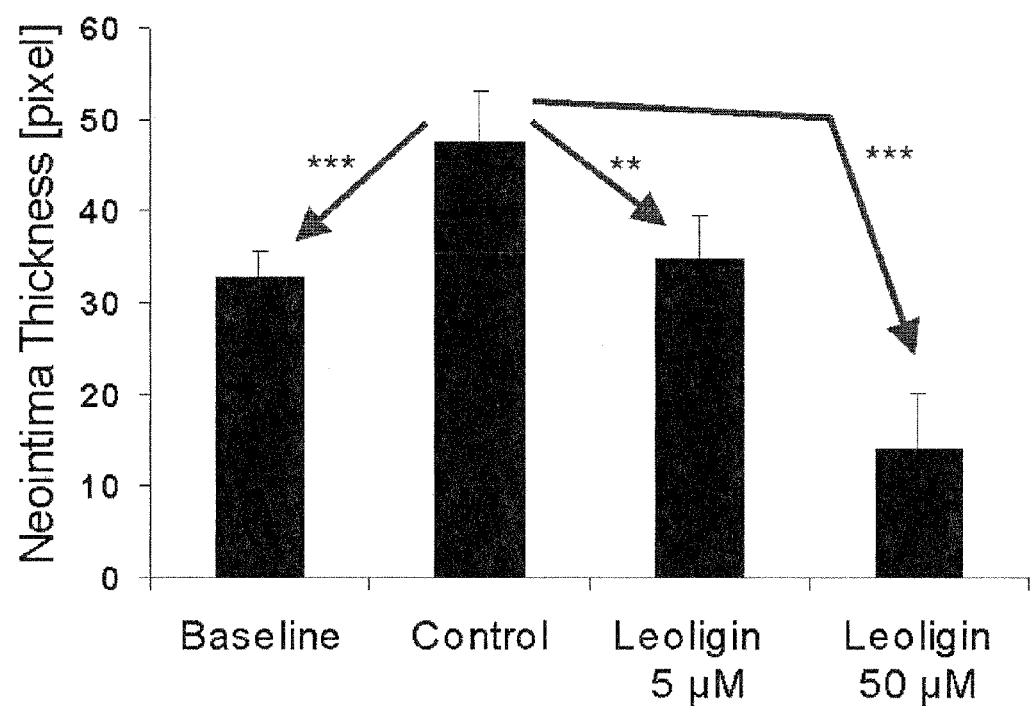
Figure 2:
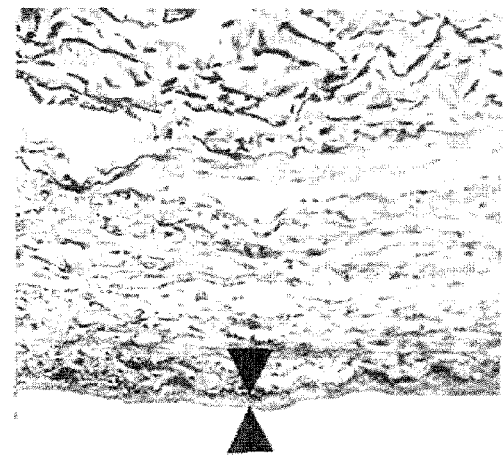
Figure 2:
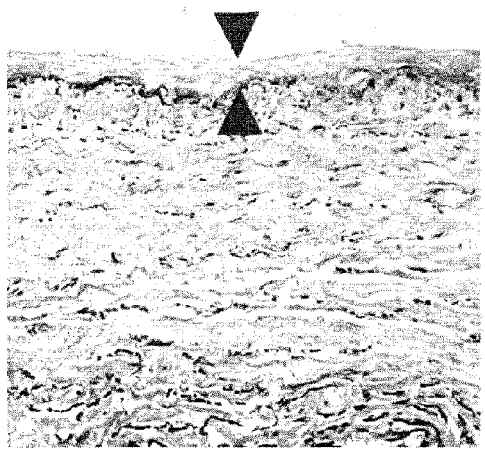
Figure 2:
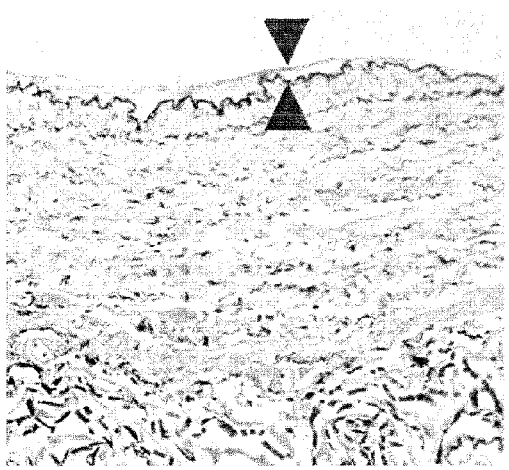
Figure 2:
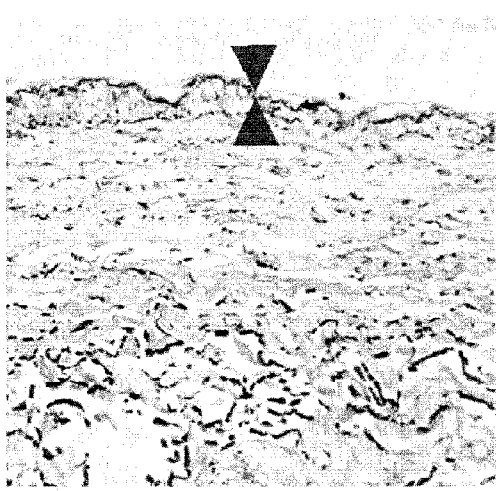

FIG. 2. Leoligin inhibits intimal hyperplasia of human saphenous veins in vitro

The diagram in FIG. 2A summarises the data from experiments where human saphenous veins were induced to develop intimal hyperplasia in organ culture. Tissue samples were incubated with DMSO (solvent control) or various concentrations of leoligin for 2 weeks. After the incubation tissues were fixed, dehydrated, and embedded in paraffin. After preparation of sections, samples were stained (Elastica van Giesson stain), and the intimal thickness was measured using Image J software. Approximately 30 measurements per sample and a total of 5 samples (different donors) per concentration were analysed. Shown are mean values (in pixel) +/−S.D. Baseline samples were fixed directly after preparation of fresh tissue and represent the status of the vessel prior to organ culture.

... $p<0.01$; * ... $p<0.001$.

FIG. 2B shows the effect of the presence or absence of leoligin on organ culture-caused intimal thickening of a representative sample of a saphenous vein with mild pre-existing intimal hyperplasia (upper row, left: baseline; upper row, right, control; lower row, left: leoligin 5 µM; lower row, right: leoligin, 50 µM). The area between the arrows indicates the intimal thickness.

Figure 3:
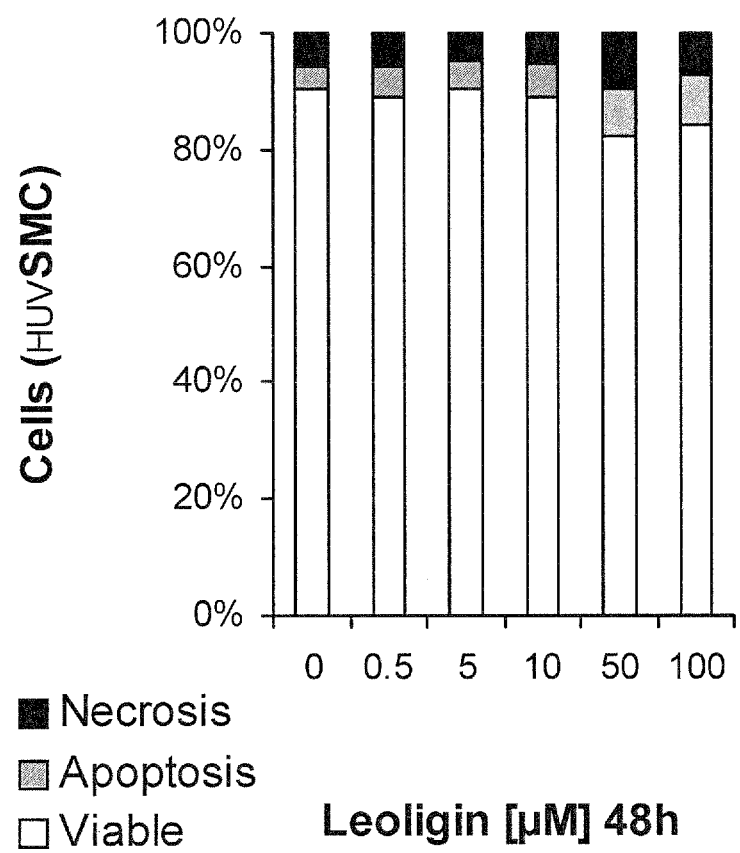
Figure 3:
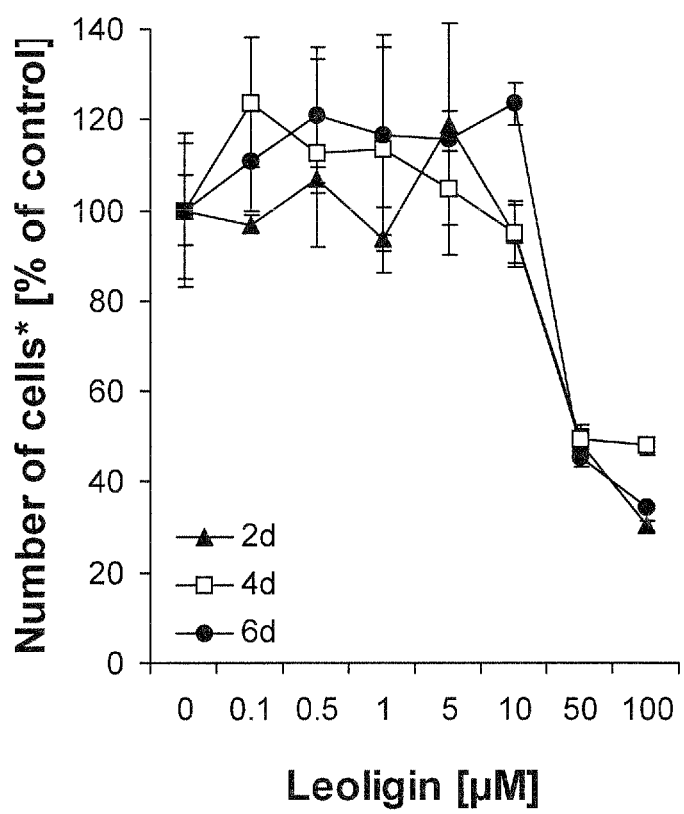
Figure 3:
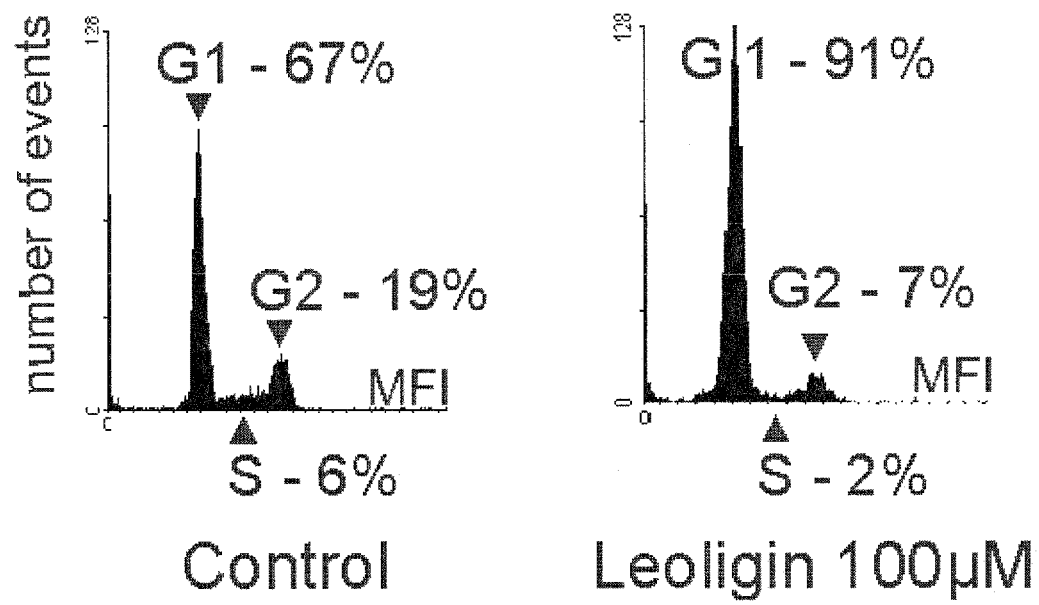
Figure 3:
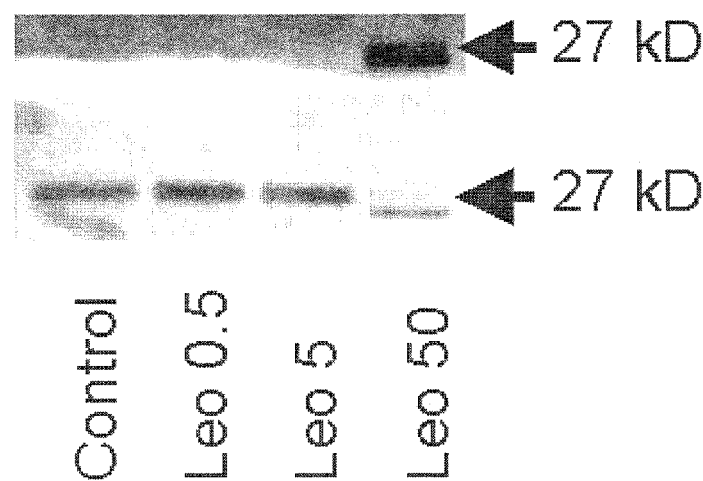

FIG. 3. Leoligin inhibits SMC proliferation, induces a cell cycle arrest in the G1 phase and leads to an accumulation of p27/KIP In order to investigate the effect of leoligin on the cellular level, isolated primary human vascular smooth muscle cells (SMCs) were incubated with the indicated concentrations of leoligin for the indicated times. The diagram in FIG. 3A shows an analysis of cell viability determined by the annexin V/propidium iodide method and FACS analyses. Values shown are mean values from a representative experiment performed in triplicates. The diagram in FIG. 3B shows an analysis of cell proliferation by the XTT assay. Values shown are mean values from three independent experiments +/−S.D. The histogram blots in FIG. 3C show the results from a DNA content analysis of control-treated or leoligin-treated SMCs after 24 hours of incubation (upper row, left histogram . . . solvent control; upper row, right histogram . . . leoligin). The Western blot (lower row) shows an analysis of p27/KIP of SMCs incubated with leoligin for 24 hours with the indicated concentrations of leoligin.

Figure 4:
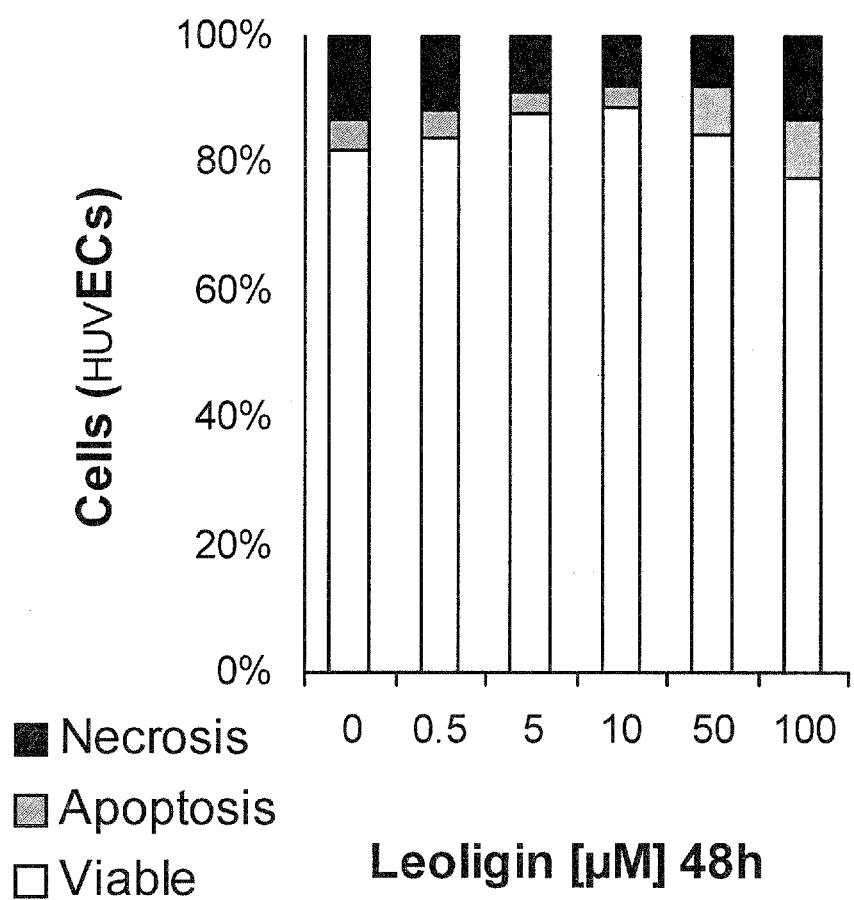
Figure 4:
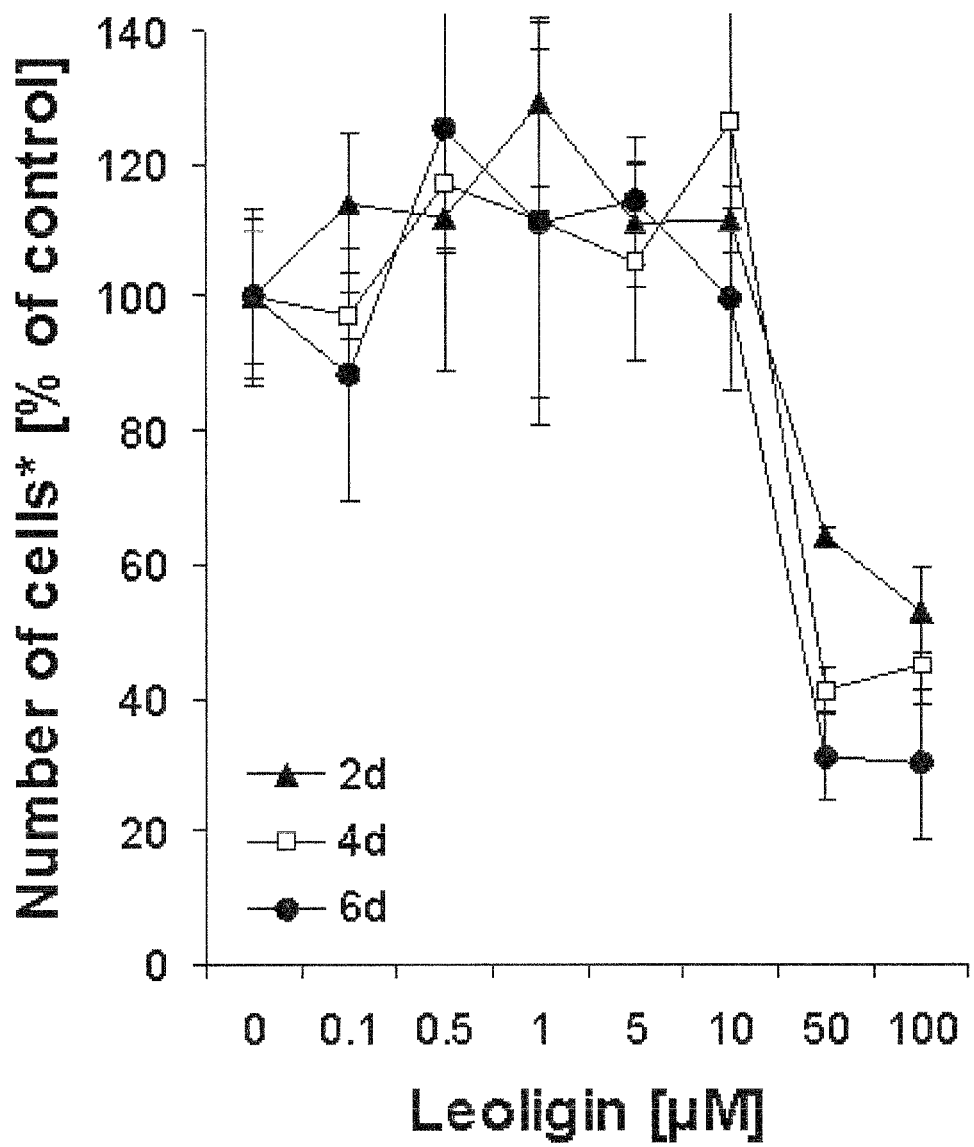
Figure 4:
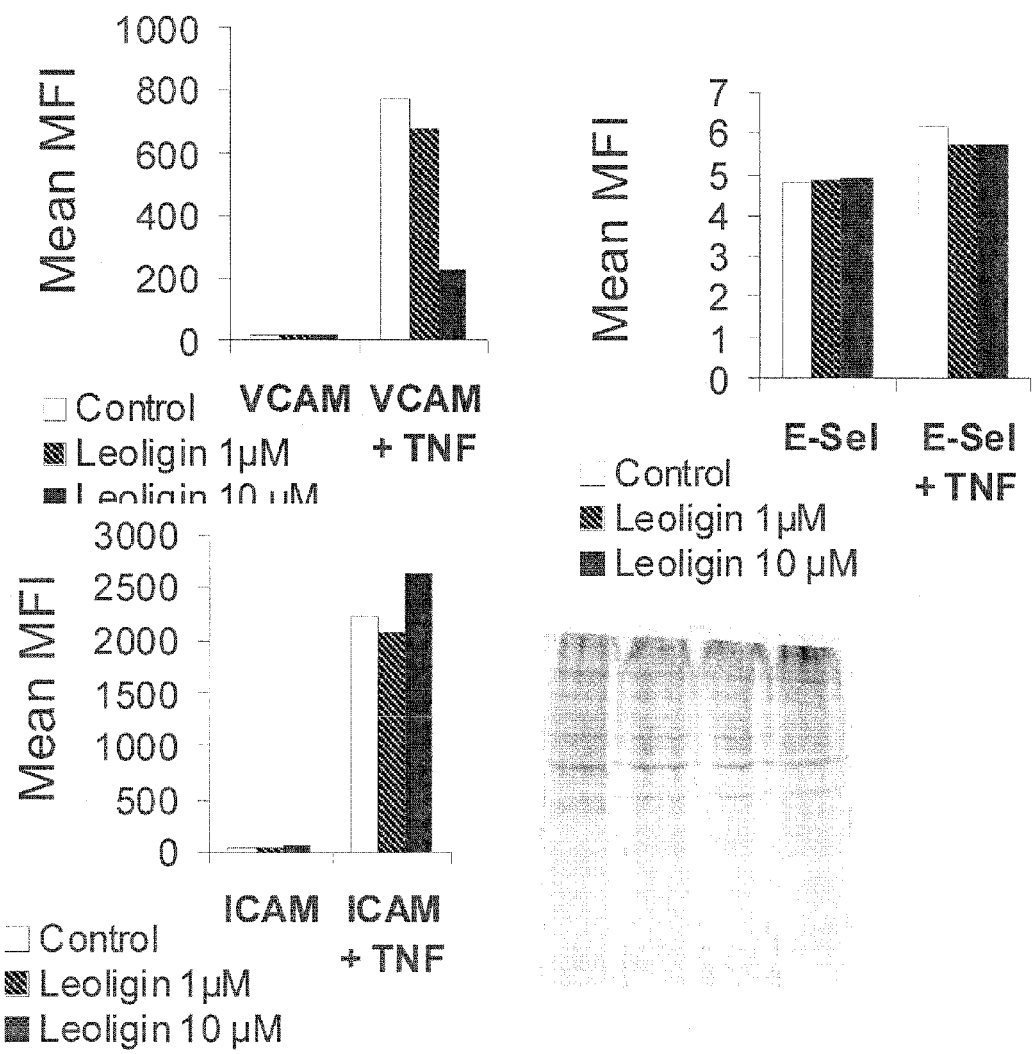

FIG. 4. Leoligin is not toxic for ECs and inhibits TNFalpha-mediated VCAM expression.

The effects of leoligin on endothelial cells is shown in FIG. 4. Primary human vascular endothelial cells (ECs) were incubated with the indicated concentrations of leoligin for the indicated times. The diagram in FIG. 4A shows a representative analysis of cell viability determined by the annexin V/propidium iodide method and FACS analyses. Values shown are mean values from a representative experiment performed in triplicates. The diagram in FIG. 4B shows an analysis of EC proliferation by the XTT assay. Values shown are mean values from three independent experiments +/−S.D. The impact of leoligin on TNFalpha-induced surface expression of VCAM-1, ICAM-1, and E-selectin (E-Sel) is shown in the three diagrams in FIG. 4C. Data shown are mean fluorescence intensities (MFI) of representative experiments. The lower right image in FIG. 4C shows a metabolic protein labelling analysis of EC in the presence of the indicated concentrations of leoligin. After protein preparation, total cellular proteins were separated on polyacrylamide gels, gel were dried and analysed by exposure to x-ray films.

Figure 5:
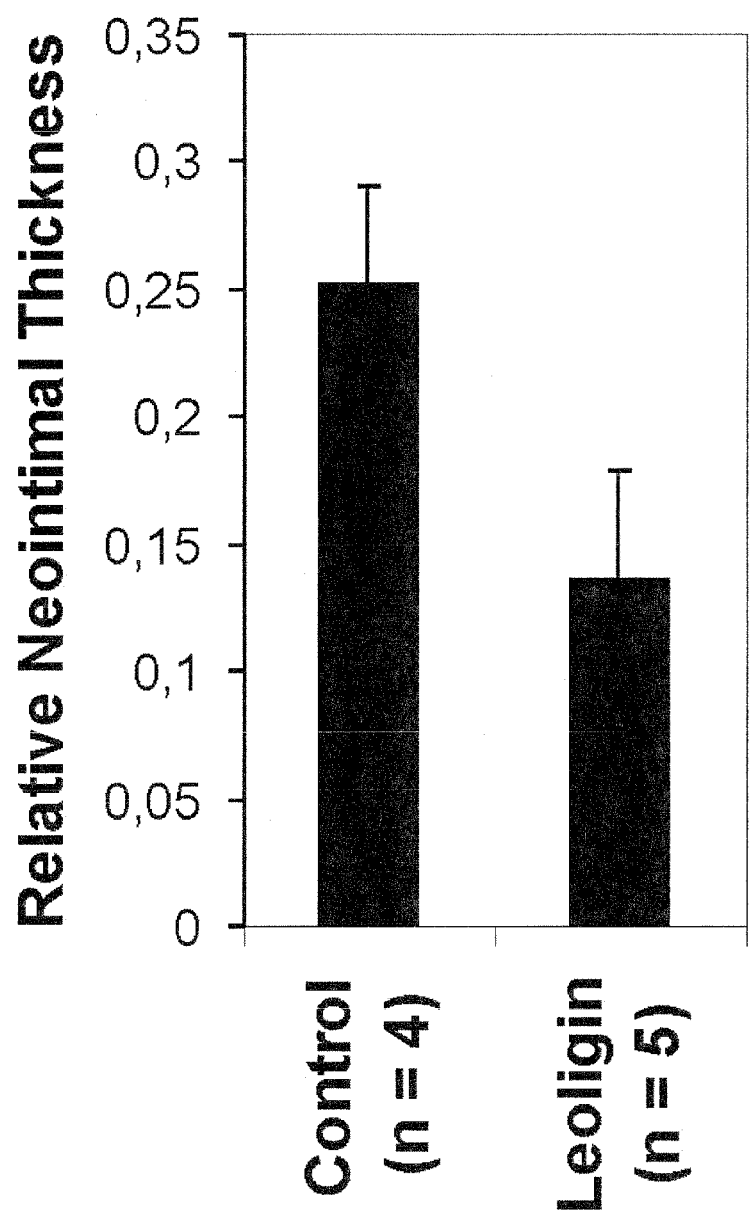
Figure 5:
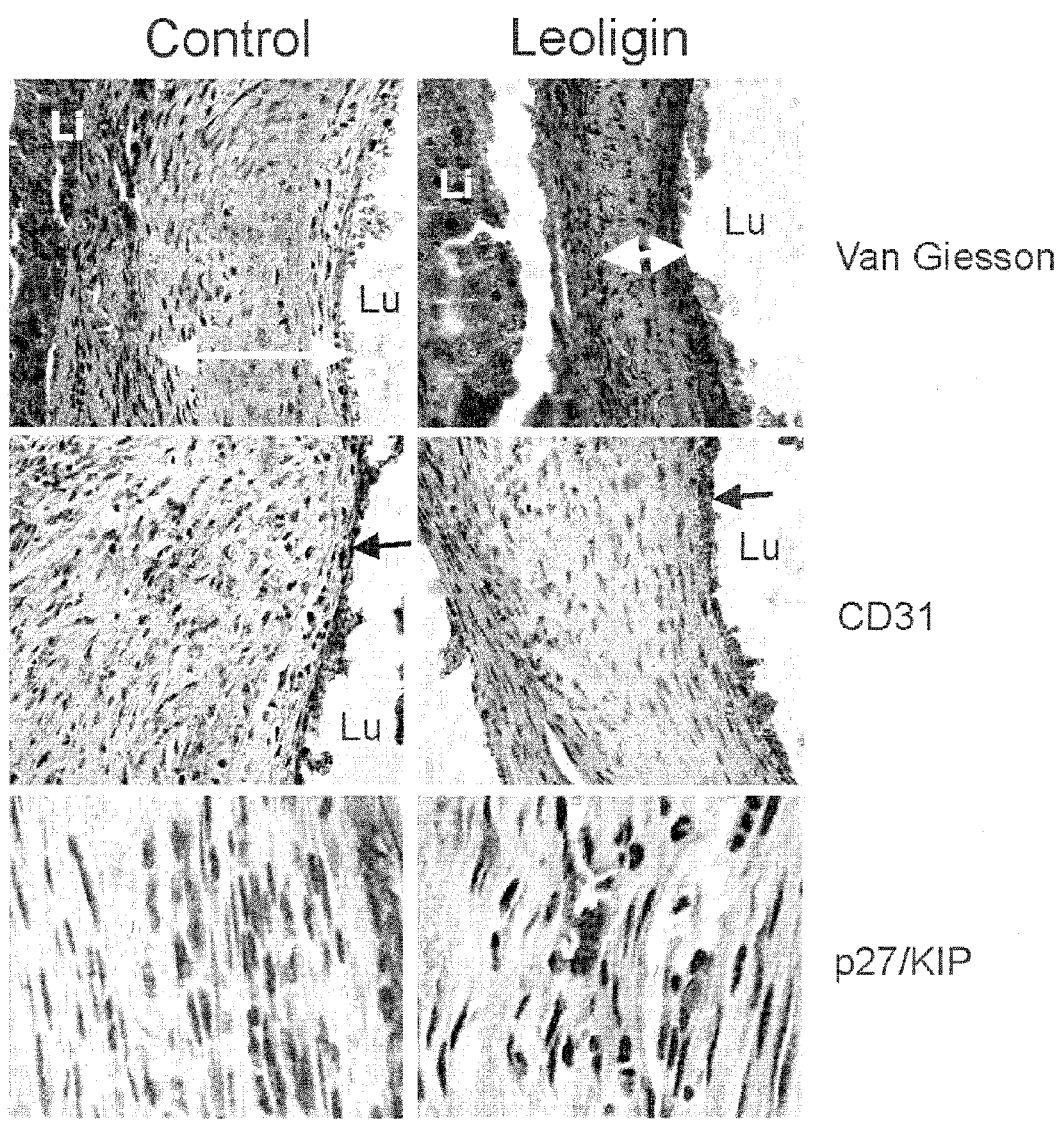

FIG. 5. Leoligin inhibits neointima formation in vivo, without causing endothelial damage.

The effects of leoligin on intimal hyperplasia of venous bypass conduits in vivo are shown in FIG. 5. The diagram in FIG. 5A displays a morphometric analysis of intimal thickness of vena cava interposed into the carotid artery of control-treated animals and leoligin-treated animals. Before wound closure after the transplantation, a peradventitial depot of 100 p. 1 of 0.9% NaCl (control) or 100 μl of 100 μM leoligin in 0.9% NaCl were applied. After 4 weeks conduits were removed and subjected to morphometric analyses and to immunohistochemistry. FIG. 5B: the upper two images show a Elastica van Giesson stain of sections of the venous conduits. White arrows indicate neointimal thickness which was analysed by morphometry (see FIG. 5A). Central images display a staining for the endothelial cell CD31/PECAM-1 antigen (brown, black arrows) combined with a hematoxilin stain. Lower images display a immunohistochemical staining of the sections for the cell cycle inhibitor p27/KIP-1 (brown) combined with a hematoxilin stain. The abbreviations "Lu" and "Li" stand for the full terms "lumen" and "liver", respectively.

Figure 6:
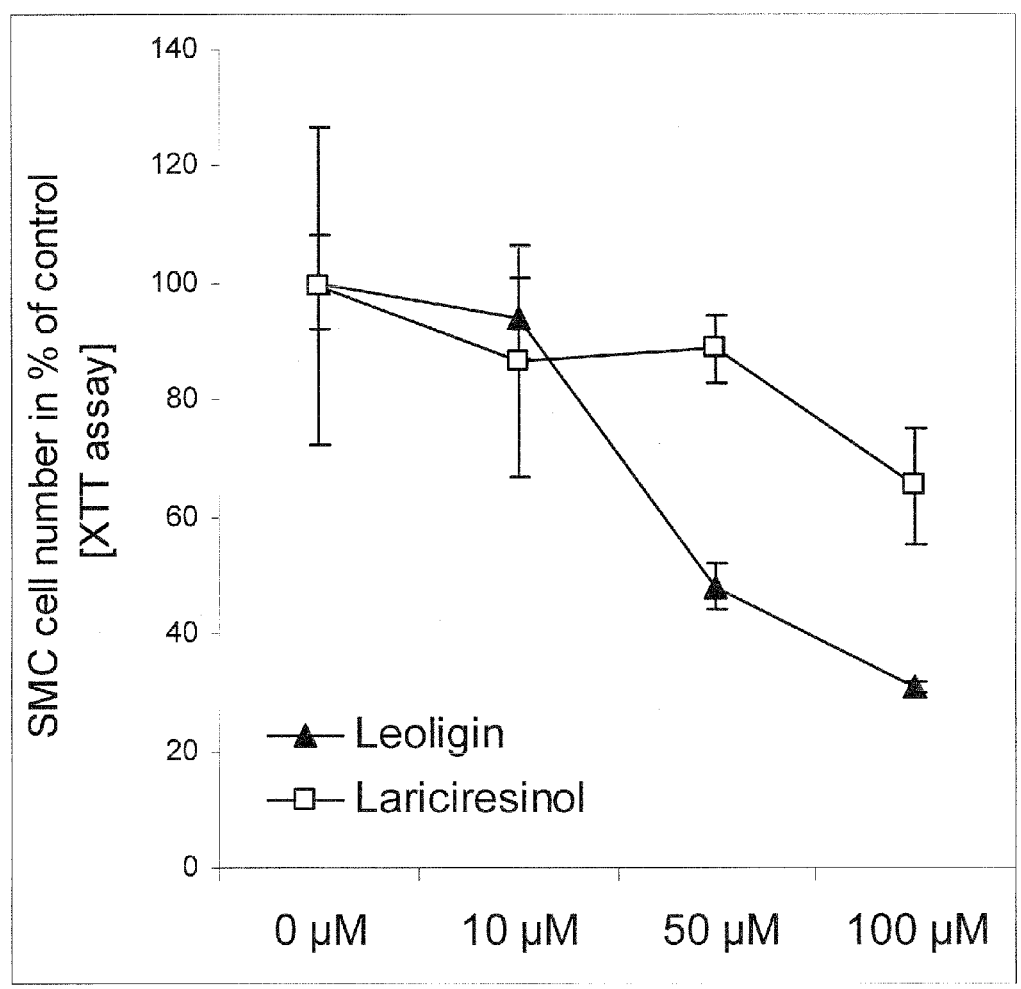

FIG. 6. SMC comparison

The diagram in FIG. 6 shows a comparison of the smooth muscle cell (SMC) proliferation-inhibitory activity of lariciresinol and leoligin by the XTT assay. Values shown are mean values from three independent experiments +/−S.D.

Figure 7:
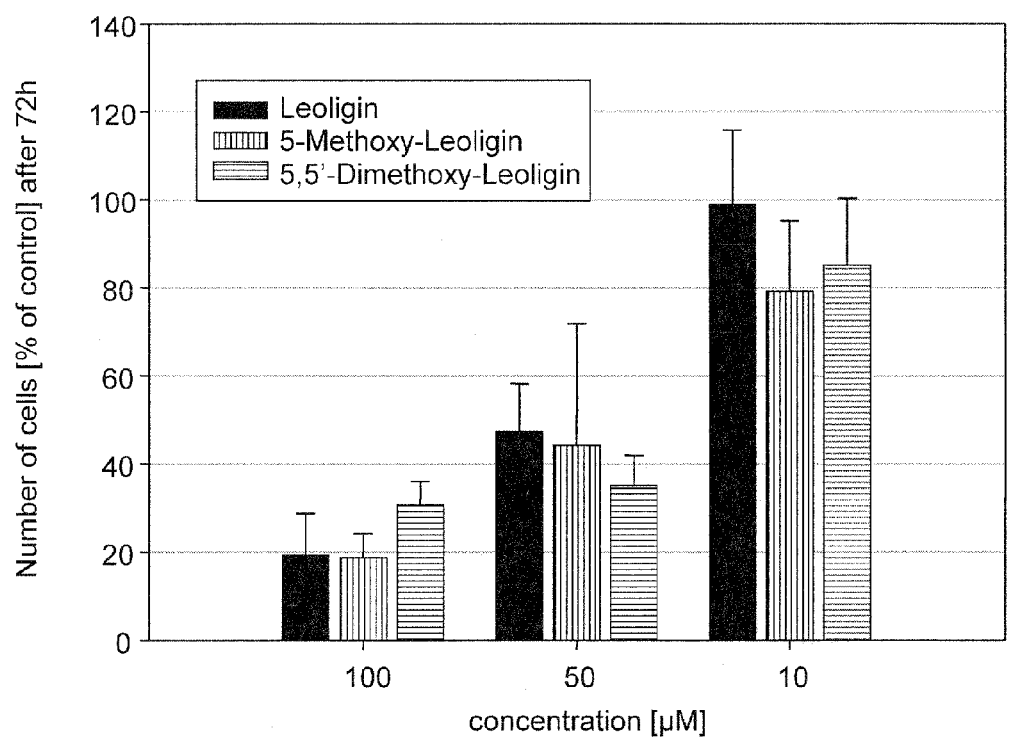

FIG. 7. SMC comparison

The diagram in FIG. 7 shows a comparison of the smooth muscle cell (SMC) proliferation-inhibitory activity of leoligin and the two indicated derivatives by the XTT assay. Values shown are mean values from three independent experiments +/−S.D.

FIG. 8. Pathway

FIG. 8 shows a possible synthetic pathway of leoligin.

The following Examples illustrate the invention.

EXAMPLE 1

Leoligin Inhibits Intimal Hyperplasia of Venous Bypass Grafts

Material and Methods
General

All reagents used were of purissimum or analytical grade quality and were purchased from Sigma Aldrich (Sigma-Aldrich, Vienna, Austria) if not specified otherwise. Water was produced by reverse osmosis followed by distillation.

Plant Material, Isolation, and Purification of Leoligin

Ground roots (1907.84 g) from *L. alpinum* Cass. were exhaustively macerated with dichloromethane (12.5 l DCM, at RT, eight times). Voucher specimens are deposited at the herbarium of the Institut für Pharmazie/Pharmakognosie, Leopold-Franzens-Universität Innsbruck. Extracts were evaporated to dryness yielding 43.0 g crude dichloromethane extract. 40.0 g of the obtained crude extract were redissolved in 100 ml MeOH and separated in a MeOH soluble and insoluble part. The soluble part was separated by Sephadex® LH 20 (Pharmacia Biotech, Sweden) CC (90×3.5 cm) with MeOH as mobile phase yielding 8 fractions. Fraction 5 (15.13 a; 320-410 ml elution volume) was rechromatographed by silica CC (180 g, 41×3.5 cm) using a PE-acetone gradient with an increasing amount of acetone yielding 40 fractions (A-1 to A-40). A small amount (28.2 mg) of Fraction A-21 (PE/acetone. 85:15: 441.2 mg) was separated by semi preparative HPLC (Phenomenex Synergy Max-RP column (10 μm. 10×250 mm): 55% acetonitrile/45% water, isocratic; flow: 3.50 ml/min; 25° C.) yielding 16.0 mg pure leoligin and i4.0 mg of its 5-methoxy derivative. A small amount (26.5 mg) of Fraction A-22 (PE/acetone. 85:15: 77.8 mg) was separated by semi preparative HPLC (Waters X-Terra Prep MS C18.5 μm, 7.8×100 mm column; 70% MeOH/30% water, isocratic; flow: 1.50 ml/min; 25° C.) yielding 6.3 mg of the 5,5'-dimethoxyderivative of leoligin.

Preparation of Extracts Enriched in Leoligin and its Methoxy-derivative

In order to quantify the content of leoligin and its methoxy-derivative in different extract preparations several extraction procedures were used. Therefore ground roots (20.00 g) from *L. alpinum* Cass. were exhaustively macerated with dichloromethane (100 ml DCM, at RT, eight times). After filtration the obtained extracts were combined, evaporated to dryness to yield a semi solid DCM-extract. Other extracts were prepared by ultrasonic extraction using 20.00 g ground roots which were sonicated for 15 min using 1×200 ml and 1×100 ml of solvent or a second ultrasonic extraction cycle after air drying of the plant material (5.00 g; 2×15 min; 2×100 ml solvent). The leoligin content was determined by means of HPLC-quantification using the method of external standard. Each extract was prepared in duplicate and quantified in triplicate. The content of 5-Methoxy-leoligin was calculated using the calibration curve of leoligin.

Cell Culture

Human umbilical vein endothelial cells (HUVECs) were isolated from umbilical cords (kindly donated by the Gynaecology and Obstetrics Department, Innsbruck Medical University) by enzymatic detachment using collagenase, as previously described; see Bernhard, *FASEB J* 17(15), 2302-4 (2003). Human umbilical vein smooth muscle cells (SMCs) were isolated from the same umbilical cords according to Chamley-Campbell, *Physiol Rev* 59(1), 1-61 (1979). SMCs were routinely passaged in 0.2% gelatine-coated (Sigma, Steinheim, Germany) polysterene culture flasks (Becton Dickinson, Meylan Cedex, France) in Medium 231 (Cascade Biologics, Paisley, UK). The isolation and analysis of human umbilical cord ECs and SMCs has been approved by the Ethics Committee of the Innsbruck Medical. University.

Quantification of Cell Death and Cellular DNA Content

For detection and/or quantification of cell death, forward/sideward light scattering analysis, the Annexin V-propidium iodide method, and staining of nuclear DNA content (cell cycle analyses) were used as described; see Bernhard *FASEB J* 13(14), 1991-2001 (1999).

Analysis of Cellular Proliferation

Cell proliferation was measured by the XTT cell proliferation assay (Biomol, Hamburg, Germany) as described by the manufacturer. The XTT assay is based on the ability of metabolic active cells to reduce the tetrazolium salt XTT to orange coloured compounds of formazan. The dye formed is water soluble and the dye intensity can be read at a given wavelength with a spectrophotometer. The intensity of the dye is proportional to the number of metabolic active cells. In addition to the XTT assay all proliferation-experiments were also evaluated by counting cells in a coulter counter.

Surface Expression Analyses ICAM, VCAM, and E-selectin.

FACS-based analyses of surface adhesion molecule expression was performed according to a protocol by Gräbner et al. (see Grabner, *Cytometry* 40(3), 238-44 (2000). Antibodies used were anti-VCAM-1 antibody (clone 1.4 C3, Neomarkers), anti-ICAM-1 antibody (clone 28, DAKO Cytomation), and anti-E-selctine antibody (clone 16G4; Novo castra).

Western Blotting

Western blotting was performed as previously described; see Bernhard, *Cell Death Differ* 8(10), 1014-21 (2001). Primary antibodies used were anti-p27/KIP-1 antibody (clone 57; BD Transduction Laboratories).

Metabolic Labelling of Proteins

Metabolic labelling with $^{35}$S-methionine/cysteine was performed as previously described (Bernhard (2001), loc. cit.).

Human Saphenous Vein Organ Culture

For organ culture experiments, remnants (surgical waste) of saphenous veins from patients undergoing CABG were collected. The saphenous veins were opened longitudinally and attached to silicone patches (with the endothelium facing upwards). Tissue pieces were incubated with culture medium (RPMI1640, 30% serum, 8 heparin mU/ml, antibiotics) for 2 weeks in the presence or absence of leoligin, to induce intimal hyperplasia. For details see Schachner, *Eur J Cardiothorac Surg* 32, 906-911 (2007). Leoligin was added freshly every second day to organ cultures over a time period of 2 weeks. 5 µM leoligin completely inhibited intimal hyperplasia (p=0.003), and 50 µM even reversed pre-existing intimal hyperplasia of saphenous veins (p<0.001). The use of human saphenous veins has been approved by the Ethics Committee of the Innsbruck Medical University.

Mouse Model—Vein Graft Disease

In the applied mouse model the vena cava of a donor mouse was interposed into the carotid artery of a recipient mouse. After transplantation and prior to wound closure a 100 µl depot of 0.9% NaCl (control group) or 100 µM leoligin in 0.9% NaCl (leoligin group) was placed around the adventitia of the vein graft in the recipient mouse. 4 weeks after the intervention mice were sacrificed and the interposed venae cavae were harvested for analyses. Of the 7 animals per group 3 control and 2 leoligin-treated animals showed no blood flow due to thromboses after 4 weeks and were consequently excluded from further analyses. For details on the surgical procedure see Schachner, *Eur J Cardiothorac Surg* 30(3), 451-63 (2006); Schachner, *Heart Surg Forum* 9(1), E515-E517 (2006). Animal experiments were approved by the Commission for Animal Testing Affairs of the Austrian Ministry for Science and Research.

IHC and Morphometric Analyses

Following fixation in 4% paraformaldehyde and dehydration of tissues from organ culture and mouse experimentation, tissues were embedded in paraffin (venae cavae from the in vivo experiments were embedded into mouse liver prior to fixation) and sections were prepared. Immunohistochemistry was performed with the Accustain Elastica Stain (HT25) kit (Sigma-Aldrich, USA) or the En Vision+System–HRP (DAB) (DakoCytomation, Denmark) according to the manufacturers instructions. Primary antibodies used were anti-p27/KIP-1 antibody (clone 57; BD Transduction Laboratories), and anti-CD31/PECAM-1 antibody (clone JC70A, Dako Cytomation). Image analyses were performed using the Image J software of the National Institute of Health (USA).

Results

Preparation of Extracts Enriched in Leoligin and Ist Methoxy-derivates

Root extracts comprising leoligin and its derivates 5-Methoxy-leoligin and 5,5'-dimethoxy-leoligin have been prepared as described herein above (i.e. roots macerated at room temperature and extracted using dichlormethane), whereby the yield of the extract lies typically in the range of between 1.03 his 2.26% and whereby the maximum level of the leoligin and methoxy-leoligin content (quantified as a mixture thereof) is 2.14%.

In order to obtain extracts enriched in leoligin and its derivates, the plant material is in a first step extracted with hexane or heptane followed by a subsequent extraction with organic solvents dicholoromethane, chloroform or ternary butyl methyl ether. The results are summarized in the table below.

| Pretreatment solvent (defatting) | Extraction solvent | Yield of extract (w %) | Leoligin content (w %) in the extract | Total lignan content in the extract (calculated as leoligin; w %) |
| --- | --- | --- | --- | --- |
| — | dichloromethane* | 1.03-2.26% | 0.77-1.36% | 1.69-2.14% |
| — | n-hexane** | 0.07-0.15% | 0.67% | 1.47% |
| — | n-heptane** | 0.12-0.27% | 0.74% | 1.55% |
| n-hexane | dichloromethane*** | 0.50% | 1.32% | 2.67% |
| n-hexane | chloroform*** | 0.65% | 1.31% | 2.71% |
| n-hexane | tBMe*** | 0.39% | 1.19% | 2.43% |

*exhaustive mazeration (20.00 g; 8 × 100 ml);
**ultrasonic extraction (20.00 g; 15 min; 1 × 200 ml; 1 × 100 ml);
***ultrasonic extraction (5.00 g; 2 × 15 min; 2 × 100 ml).

"Yield of extract" refers to the weight of the extract vs. the basic material used, wherea leoligin content refers to the percentage by weight of Leoligin and lignan, respectively, in the extract.

The concentration of lignans (and derivatives) was also increased by the use of Sephadex-LH20-column chromatography (increase in the leoligin content from 0.77% to 2.21%). The most pronounced increase (increase in the leoligin content from 1.36% auf 9.76%) was achieved using silica gel column chromatograph (mobile phase: Petroleum ether-aceton).

Leoligin a Compound from Edelweiss Potently Inhibits Intimal Hyperplasia in a Human Saphenous Vein In vitro Model.

Leoligin [(2S,3R,4R)-4-(3,4-dimethoxybenzyl)-2-(34-dimethoxyphenyl)tetrahydrofuran-3-yl]methyl(2Z)-2-methylbut-2-enoat (see FIG. 1) a compound that was previously isolated from the roots of Edelweiss (*Leontopodium alpinum*

Cass) is a lignan type secondary plant metabolite. In our organ culture-based screen for compounds capable of inhibiting human saphenous vein intimal hyperplasia, leoligin showed a profound inhibitory activity (see FIG. 2). Leoligin when added to organ cultures over a time period of 2 weeks (added freshly every second day) inhibited intimal hyperplasia in a dose-dependent fashion. 5 µM leoligin completely inhibited intimal hyperplasia (p=0.003), and 50 µM even reversed pre-existing intimal hyperplasia of saphenous veins (p<0.001) (see FIG. 2).

Leoligin Inhibits SMC Proliferation by Inducing a Cell Cycle Arrest in the G1Phase which is Associated by a Shift in Molecular Weight and an Accumulation of p27/KIP Protein In order to reveal the mechanism underlying leoligin-mediated inhibition and reversal of saphenous vein intimal hyperplasia we analysed the effects of leoligin on isolated primary human vascular smooth muscle cells, which represent the central cell type in intimal thickening and intimal hyperplasia (SMC proliferation, and migration). Our analyses clearly showed that leoligin causes only a marginal increase in cell death (apoptosis and necrosis) in SMCs after 48 hour (FIG. 3, upper panel, left side). Analyses at later time points were consistent with the findings after 48 hours (data not shown). In contrast, analyses of cell numbers by the XTT proliferation assay (FIG. 3, upper panel, right side) as well as by Casy-based cell counting (data not shown) revealed a significant SMC proliferation inhibitory effect of leoligin. Consequent measurements of nuclear DNA content (FIG. 3, two lower panels, left side) revealed that leoligin causes a massive accumulation of cells in the G1-phase of the cell cycle. Since it is well known that a number of cell cycle regulators can cause a G1 arrest, we performed a Western blot based analyses for changes in G1 arrest-relevant cell cycle regulators. The lower right panel of FIG. 3 shows a Western blot demonstrating that leoligin induces a complete change in the appearance of p27/KIP protein i.e. from one signal at 27 kD to an intensive signal at 58 kD, and three weak signals at 24, 27 (original signal) and 85 kD (the 85 kD signal was hardly visible and is not shown). The accumulation of p27/KIP is well known to mediate a G1-arrest by binding to and thereby inactivating the cyclinD1/E-cdk2 complex. The observed shift in molecular weight may indicate the binding of p27/KIP to this complex or an oligomerisation of p27/KIP molecules.

Leoligin is not Toxic for ECs and Inhibits TNFalpha-mediated VCAM-1 Expression.

Since the integrity of the vascular endothelium plays a central role in vascular repair and healing, anti-thrombosis, and the graft atherosclerosis-relevant control of cell (macrophages) and compound (cholesterol) exchange between the blood and the vessel wall we also analysed the effects of leoligin on the vascular endothelium. Although leoligin also inhibited the proliferation of ECs no toxic or cell death-inducing effect of leoligin on ECs could be observed (see FIG. 4, left panels). Analyses at later time points were consistent with the findings after 48 hours (data not shown). Interestingly, leoligin inhibited TNFalpha-mediated surface expression of VCAM-1 (upper right panel). To exclude that general phenomena, like an inhibition of the endothelial translational machinery by leoligin accounts for this observation, we performed metabolic protein labelling experiments (FIG. 4, lower right panel), and analysed the effect of leoligin on other adhesion molecules (FIG. 4, right side, two central panels). These data demonstrate that leoligin does not block protein synthesis, and does not interfere with the translocation of proteins to the cellular surface in general, but specifically inhibits stimulated VCAM-1 expression on the EC surface.

Leoligin Inhibits Neointima Formation in vivo, without Causing Endothelial Damage.

To test the applicability of leoligin in vivo we analysed leoligin effects in a mouse model for vein graft disease (see Methods section). Like in human saphenous vein bypass conduits the transplant develops a severe intimal hyperplasia within a couple of weeks. Leoligin was applied directly after the transplantation as a periadvential reservoir (100 µl of 100 µM leoligin in 0.9% NaCl) before surgical closure of the wound. Four weeks after the transplantation mice were sacrificed and the venous conduits were removed for further analyses. Thrombosed veins were excluded form further analyses (see Methods section) and the remaining samples were analysed by means of immunohistochemistry. FIG. 5 (left side) shows that leoligin treatment, in contrast to control-treatment (0.9% NaCl), potently inhibited intimal hyperplasia in vivo. Vein grafts of mice treated with leoligin showed significantly reduced neointimal thickness (upper central and upper right image). A CD31 (endothelial marker) staining of the sections revealed that the endothelial layer of leoligin and control treated conduits was intact. Finally, a p27/KIP staining of the sections revealed that a large number of cells/nuclei in the leoligin-treated grafts stained positive for p27/KIP even four weeks after the application of leoligin, indicating a long duration of drug effect.

In the in vivo experiments described herein above leoligin was added directly after the surgical procedure. Thereafter, mice were kept for additional 4 week, only then samples were analysed. Since a large number of SMCs in the leoligin group stained positive for p27/KIP the mechanism via which leoligin inhibits the proliferation of SMCs may be the induction of differentiation. In contrast to cell culture and in vivo experiments where leoligin was added only once and at the beginning of the experiments, leoligin showed profound inhibition of intimal hyperplasia in the in vitro organ culture experiments (leoligin was added every second day) already at a concentration of 5 µM. These data suggest that a constant addition of leoligin may improve the results but also that a positive therapeutic effect can be achieved by a single application of leoligin, the consequence of which being detectable even 4 weeks after this application in vivo. With respect to the used of saphenous veins with pre-existent intimal hyperplasia for CABG, leoligin may help to increase patency rates simply by applying leoligin to the grafts prior to re-implantation. In addition, differences in the potential to inhibit or reverse intimal hyperplasia by varying the dose and duration of treatment, may help to reduce complications e.g. graft aneurysms which may occur as a result of reduced adaptive tissue remodelling in the vessel wall.

The above provided assessment using an in vivo mouse model for vein graft disease can also be carried out in larger animals/animal models. An exemplary protocol (experimental set up and evaluation of data) using a porcine animal model (i.e."Landschwein") to assess the efficacy of the particular compound known under the trivial name "Leoligin" is given herein below.

Experimental Setup

Leoligin is used in a concentration of 100 µM. Animals are separated into two treatment groups (control, treatment). Furthermore, animals are separated into groups for a harvesting time point after 4 weeks and 12 weeks, respectively. The treatment schedule is illustrated in the following table:

|  | Compound tested | Time of analysis (postoperativ) | Number of animals |
|---|---|---|---|
| Treatment group 1 | | | |
| Control | NaCl | 4 weeks | 6 |
| Leoligin | NaCl + Leoligin | 4 weeks | 6 |
| Total | | | 12 |
| Treatment group 2 | | | |
| Control | NaCl | 12 weeks | 6 |
| Leoligin | NaCl + Leoligin | 12 weeks | 6 |
| Total | | | 12 |

Anaesthesia and Surgical Procedure—Vena Saphena as Carotis Graft in the "Landschwein" (Pig Race)

For transportation and to prevent narcosis complications animals receive in the cot an intramuscular injection of 4 mg/kg Azaperon and 0.1 mg/kg Atropin one hour prior to narcosis. Sleeping animals are transported in a transport box with straw filler to the operating theatre. Animals receive an infusion of 2-3 mg/kg Propofol and 15 mg Piritramid via the ear vein, followed by intubation and ventilation with 30% $O_2$. Animals receive an initial muscle relaxation 8 mg Pancuronium and repeatedly 0.2 mg/kg/h Pancuronium. For maintenance of narcosis animals receive a permanent infusion of 8-12 mg/kg/h Propofol and 15 mg Piritramid. In order to prevent pain in the animals the dose may be increased. During the preparative phase animals receive in addition to the above a permanent infusion with 6 ml/kg/h of Ringer-Lactate.

Surgical Procedure: Carotis-graft

After the initiation of anaesthesia according to the above protocol animals are kept in dorsal position, shaved, washed with Octinsept for disinfection, and covered with sterile cloth. For preparation of the saphenous vein a ca. 10 cm longitudinal incision is made on the hind leg of animals. Following the identification of the vein, the vein is cleaned from surrounding tissue by "no-touch"-technique. Side arms are clipped and cut through. After the preparation of the vein by the above technique, the vein is removed and canulated via the distal end. To test for tightness and to expand the vessel diameter to the proper size, the vein is expanded by flushing with a pressure of 80-100 mmHg. Flushing and expansion of the sephenous vein in control animals is done using 0.9% NaCl-solution including 1‰ DMSO, in the treatment group a 100 μM leoligin (or derivative thereof) solution in 0.9% NaCl-solution including 1‰ DMSO is used (leoligin/derivative is first solubilised in DMSO (100 mM solution) and is then diluted 1:1000 in 0.9% NaCl-solution.). After expansion, veins are incubated for 30 minutes to one hour at room temperature in the above solutions. After hind leg wound closure, the surgeon starts with the preparation of the neck region. First an incision is placed on the right jugular side medial of the musculus sternocleidomastoideus. After a blunt preparation and cut through of the platysma the trionum caroticum is identified. Under protection of the vena jugularis interna and nervus vagus, the arteria carotis communis is prepared, and a 3 cm segment is isolated. Then 100 units of heparin/kg are injected intravenously. After placing of a vessel clamp at the proximal and distal side of the segment. the arteria carotis communis is cut through and the surgical margin is trimmed to an angle of 45°. A part of the prepared isolated vena saphena magna is shortened to the corresponding length and is anastomosed on both sides by an end-end technique. The anastomose is sutured with 7/0 Prolene in continous technique. To increase the exposure time of the vessel to leoligin (or derivative), resorbable haemostypticum (Dabostemp clothes) are soaked with 0.9% NaCl-solution including 1‰ DMSO (control), or a 100 μM leoligin (or derivative) solution in 0.9% NaCl-solution including 1‰ DMSO (treatment group) are warped around the interposed vein. The wound is closed in layers, then the skin is closed. To keep the number of animals low the same procedure is repeated on the left side according to the above protocol. After surgery, animals are transported to the animal keeping facility in a species appropriate manner and receive a pain therapy for additional 7 days with Dipidolor and Novalgin.

Harvesting—Surgery

Harvesting is performed 4 and 12 weeks after surgery. Anaesthesia and transport, washing and covering with sterile clothes is accomplished as described above. First the surgical scar on the right side is located and the site is re-opened. After the preparation of the interposed vein vessel claps are places on the proximal and distal site, the vein is removed. The same procedure is accomplished on the left side. Animals are euthanized with a bolus of Dormicum and Fenta, followed by an injection of 20 mVal KCl.

Analyses

The following analyses are performed on the harvested vein graft:

Histology: VanGiessen, Oil red, HE-staining; Immunohistochemistry: β-Aktin, p27, p21, CD31, ICAM-1, VCAM-1, CD3, CD4, CD8, CD56, etc. Analysis is performed using the Image J Software. Evaluation and data analyses will be performed by blinded researchers; see Reisinger (2009) Cardiovasc Res. 82; 542-549, and Messner (2009), Arterioscler.Thromb.Vasc.Biol.

Electron microscopical analyses (SEM/TEM) of the endothelial surface and the composition of the vessel wall; see Messner (2009), Arterioscler.Thromb.Vasc.Biol., and Bernhard (2003), FASEB J. 17:2302-2304.

Contractillity and functionality of grafts are analysed in an organ bath; see Hammerer-Lercher A, Clin Sci (Lund). 2006; 111:225-231. Prior to harvesting the intima media thickness of grafts is analysed by sonography; see Knoflach (2003) Circulation.; 108:1064-1069, and Knoflach (2009) Stroke; 40:1063-1069.

Collection of blood and serum samples for the detection of the test compound (i.e. leoligin).

Based on the above analyses, the following parameters/effects define independently of each other a treatment success by Leoligin (or derivative): 1) An intima thickness and/or intima-media thickness of the treatment group below the control group. 2) A smaller number of smooth muscle cells in the intima of the treatment group compared to the control. 3) The presence of a higher number of p27 and or p21 positive cells in the treatment group compared to the control. 4) A smaller degree of neointima formation in the treatment group compared to the control. 5) A reduced presence of tissue remodelling processes in the treatment group compared to the control. 6) A lower number of pro-inflammatory cells in the vessel wall in the treatment group compared to the control. 7) An intact endothelium. 8) A physiological degree of contractility of the vessels. 9) A low degree of adhesion molecule expression on the endothelial surface. 10) patency of grafts and no signs of thrombus formation. 10) Conserved elasticity of grafts in the treatment group compared to the control. And 11) Conserved contractility of grafts in the treatment group compared to the control.

EXAMPLE 2

Leoligin is a Stronger Inhibitor of SMC (Smooth Muscle Cell Proliferation) than Lariciresinol The diagram in FIG. 6 shows a comparison of the smooth muscle cell (SMC) proliferation-inhibitory activity of lariciresinol and leoligin by the XTT assay after 72 h. Values shown are mean values from three independent experiments +/−S.D.

The obtained IC$_{50}$ value of leoligin (54.5 µM; Cl$_{95}$: 49.4-59.4 µM) was found to be more effective than the lariciresinol (IC$_{50}$>100 µM).

Methods FIG. 6

Analysis of Cellular Proliferation

As described above (Example 1) cell proliferation was measured by the XTT cell proliferation assay (Biomol, Hamburg, Germany) as described by the manufacturer. The XTT assay is based on the ability of metabolic active cells to reduce the tetrazolium salt XTT to orange coloured compounds of formazan. The dye formed is water soluble and the dye intensity can be read at a given wavelength with a spectrophotometer. The intensity of the dye is proportional to the number of metabolic active cells.

A use of lariciresinol in the context of stent implantation has also been proposed in DE 10 2004 046 244.

EXAMPLE 3

Leoligin and its Methoxy-derivatives Inhibit SMC Proliferation

The diagram in FIG. 7 shows a comparison of the smooth muscle cell (SMC) proliferation-inhibitory activity of leoligin and its natural derivatives by the XTT assay after 72 h. Values shown are mean values from three independent experiments +/–S.D. The obtained IC$_{50}$ value of leoligin (54.5 µM; Cl$_{95}$: 49.4-59.4 µM) was found to be not significant different from those of 5' methoxyleoligin (45.9 µM; Cl$_{95}$: 37.3-53.9 µM) or 5,5-dimethoxyleoligin (IC$_{50}$48.6 µM; CI$_{95}$: 39.9-56.6 µM).

Methods FIG. 7

Analysis of Cellular Proliferation

As described above (Example 1) cell proliferation was measured by the XTT cell proliferation assay (Biomol, Hamburg, Germany) as described by the manufacturer. The XTT assay is based on the ability of metabolic active cells to reduce the tetrazolium salt XTT to orange coloured compounds of formazan. The dye formed is water soluble and the dye intensity can be read at a given wavelength with a spectrophotometer. The intensity of the dye is proportional to the number of metabolic active cells.

The invention claimed is:

1. A method for treating or ameliorating a hyperplastic disease/disorder, wherein said hyperplastic disease/disorder is intimal hyperplasia, comprising the administration of a compound of formula (I) to a subject in an amount effective to treat or ameliorate such disease/disorder:

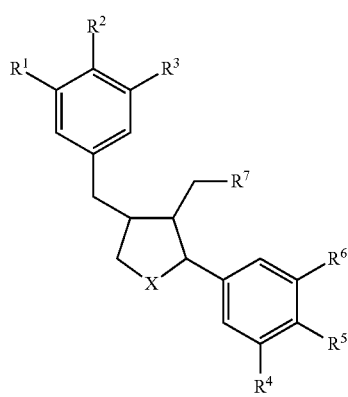

(I)

wherein

R$^1$, R$^2$ and R$^3$ are independently selected from H, OH, halogen, alkyl, or alkoxy;

R$^4$, R$^5$ and R$^6$ are independently selected from H, OH, halogen, alkyl, or alkoxy; and wherein at least one of R$^1$, R$^2$ and R$^3$ and at least one of R$^4$, R$^5$ and R$^6$ is an alkoxy group;

R$^7$ is —OC(O)R$^9$ or —C(O)OR$^9$, wherein R$^9$ is independently selected from alkyl or alkenyl; and wherein any alkyl or alkenyl group comprised in R$^7$ may be unsubstituted or substituted by one or more substituents, selected from OH, halogen or alkoxy; and X is O or S;

or any pharmaceutically acceptable salt or solvate thereof.

2. The method of claim 1, wherein the compound of formula (I) has the stereochemistry indicated in formula (Ia):

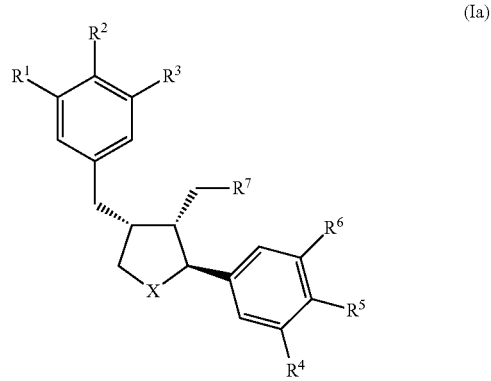

(Ia)

wherein R$^1$ to R$^7$ and X are defined as in claim 1.

3. The method of claim 1, wherein R$^7$ is —OC(O)R$^9$.

4. The method of claim 1, wherein at least two of R$^1$, R$^2$ and R$^3$ and at least two of R$^4$, R$^5$ and R$^6$ are alkoxy groups.

5. The method of claim 1,$_7$ wherein the compound of formula (I) has the following structure:

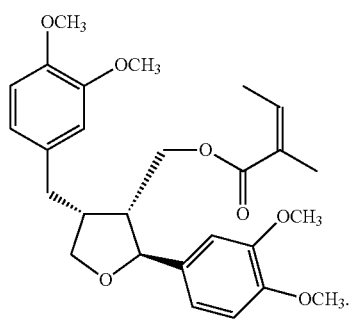 [SMILES: C/C=C(/C)C(=O)OC[C@H]1[C@@H](Cc2ccc(OC)c(OC)c2)CO[C@@H]1c1ccc(OC)c(OC)c1]

6. The method of claim 1, wherein five or all six of R$^1$ to R$^6$ are alkoxy, and the remaining group of R$^1$ to R$^6$, if applicable, is hydrogen.

7. The method of claim 1, wherein said intimal hyperplasia is stenosis or restenosis.

8. The method of claim 1, wherein said intimal hyperplasia is atherosclerosis.

9. The method of claim 1, whereby said compound is administered by any one of a parenteral route, oral route, intravenous route, subcutaneous route, intranasal route or transdermal route.

10. The method of claim 1, wherein said subject is a human.

* * * * *

UNITED STATES PATENT AND TRADEMARK OFFICE
CERTIFICATE OF CORRECTION

PATENT NO. : 8,765,804 B2
APPLICATION NO. : 13/054385
DATED : July 1, 2014
INVENTOR(S) : Hermann Stuppner et al.

It is certified that error appears in the above-identified patent and that said Letters Patent is hereby corrected as shown below:

In title page, item (56) References Cited - Other Publications, delete the 1st reference on page 1 "Back et al. "Leukotriene B4 signaling through NF-kB-dependent BLT1 receptors on vasuclar smooth muscle cells in atherosclerosis and intimal hyperlasia" PNAS, Nov. 2005, vol. 102, No. 48, pp. 17501-17506.*" and replace with --Back et al. "Leukotriene B4 signaling through NF-kB-dependent BLT1 receptors on vascular smooth muscle cells in atherosclerosis and intimal hyperplasia" PNAS, Nov. 2005, vol. 102, No. 48, pp. 17501-17506.*-- therefor.

In title page, item (56) References Cited - Other Publications, delete the 3rd reference on page 1.

In the Claims:

In claim 5, column 36, line 36, delete "The method of claim $1,_7$" and replace with --The method of claim 1,-- therefor.

Signed and Sealed this
Seventh Day of October, 2014

Michelle K. Lee
*Deputy Director of the United States Patent and Trademark Office*